`US008563526B2`

(12) United States Patent
Peng et al.

(10) Patent No.: US 8,563,526 B2
(45) Date of Patent: Oct. 22, 2013

(54) TRIAZOLE DERIVATIVES, THEIR PREPARATION AND THEIR APPLICATION IN THERAPEUTICS

(75) Inventors: Ling Peng, Marseilles (FR); Palma Rocchi, Marseilles (FR); Juan Iovanna, Marseilles (FR); Yi Xia, Marseilles (FR); Fanqi Qu, Wuhan (CN); Jinqiao Wan, Shanghai (CN); Yang Liu, Wuhan (CN); Menghua Wang, Wuhan (CN)

(73) Assignees: Institut National de la Sante et de la Recherche Medicale (INSERM), Paris (FR); Centre National de la Recherche Scientifique (C.N.R.S.), Paris (FR)

( * ) Notice: Subject to any disclaimer, the term of this patent is extended or adjusted under 35 U.S.C. 154(b) by 220 days.

(21) Appl. No.: 12/990,214

(22) PCT Filed: Apr. 29, 2009

(86) PCT No.: PCT/EP2009/055213
§ 371 (c)(1),
(2), (4) Date: Feb. 14, 2011

(87) PCT Pub. No.: WO2009/133147
PCT Pub. Date: Nov. 5, 2009

(65) Prior Publication Data
US 2011/0136754 A1    Jun. 9, 2011

(30) Foreign Application Priority Data

Apr. 30, 2008 (EP) ..................... 08155481

(51) Int. Cl.
| | | |
|---|---|---|
| *A61K 31/7056* | (2006.01) | |
| *A61K 31/4196* | (2006.01) | |
| *C07D 249/06* | (2006.01) | |
| *C07D 249/10* | (2006.01) | |
| *C07D 401/04* | (2006.01) | |
| *C07H 19/056* | (2006.01) | |

(52) U.S. Cl.
CPC ......... *A61K 31/7056* (2013.01); *A61K 31/4196* (2013.01); *C07D 401/04* (2013.01); *C07H 19/056* (2013.01)
USPC ......... 514/43; 514/383; 536/28.7; 548/266.2; 548/266.8; 548/255

(58) Field of Classification Search
None
See application file for complete search history.

(56) References Cited

U.S. PATENT DOCUMENTS

2010/0129317 A1*   5/2010   Arterburn et al. ............. 424/85.2

FOREIGN PATENT DOCUMENTS

| WO | WO 2006/004795 A | 1/2006 |
|---|---|---|
| WO | WO 2008/067002 A | 6/2008 |

OTHER PUBLICATIONS

The Oxford Textbook of Oncology, vol. 1, published 1995 by Oxford University Press, pp. 447-453.*
Pharmaceutical Dosage Forms; Tablets, second edition, vol. 2, published 1990 by Marcel Dekker, Inc, pp. 462-472.*
Braga et al., "Making Crystals from Crystals: a green route to crystal engineering and polymorphism" Chemical Communications (2005) pp. 3635-3645.*
Jain et al., "Polymorphism in Pharmacy" Indian Drugs (1986) vol. 23 No. 6 pp. 315-329.*
Vippagunta et al., "Crystalline SOlids" Advanced Drug Delivery Reviews (2001) vol. 48 pp. 3-26.*
The Merck Manual of Diagnosis and Therapy, Seventeenth Edition, published 1999 by Merck Research Laboratories, pp. 397, 398, 948, 949, 1916, 1979-1981.*
Merriam-Webster's Collegiate Dictionary, Tenth Edition, published 1998 by Merriam-Webster, Incorporated, p. 924.*
Chung, D.H. et al., Synthesis of 1-beta-d-ribofuranosyl-3-ethynyl-[1,2,4]triazole and its in vitro and in vivo efficacy against Hantavirus, Antiviral Research, Elsevier Science BV, Mar. 17, 2008, vol. 79, Issue 1, pp. 19-27.
International Search Report dated Oct. 2, 2009, for International Application No. PCT/EP2009/055213.
Moya, J. et al., In vivo effect of EICAR (5-ethynyl-1-beta-D-ribofuranosylimidazole-carboxamide) on experimental infected rainbow trout (*Oncorhynchus mykiss*) and *Coho salmon* (*Oncorhynchus kisutch*) fry with infectious pancreatic necrosis virus, Antiviral Research, Nov. 2000, vol. 48, Issue 2, pp. 125-130.
Oettle, H. et al., The role of gemcitabine alone and in combination in the treatment of pancreatic cancer, Anti-Cancer Drugs, Nov. 1, 2000, vol. 11, Issue 10, pp. 771-786.
Wan, J. et al., Discovery of novel arylethynyltriazole ribonucleosides with selective and effective antiviral and antiproliferative activity, Journal of Medicinal Chemistry, Feb. 2009, vol. 52, Issue 4, pp. 1144-1155.
Zhu, R. et al., Arylethynyltriazole acyclonucleosides inhibit hepatitis C virus replication, Bioorganic & Medicinal Chemistry Letters, Apr. 15, 2008, vol. 18, Issue 11, pp. 3321-3327.

* cited by examiner

*Primary Examiner* — Eric S Olson
(74) *Attorney, Agent, or Firm* — Knobbe Martens Olson & Bear LLP

(57) ABSTRACT

The present invention relates to novel compounds of formula (A):

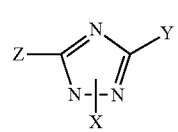

(A)

in the form of a free base or of an addition salt with an acid. The invention also relates to process of preparation of compounds of formula (A), to composition comprising them and to their application in therapeutics and in particular in cancers.

17 Claims, 7 Drawing Sheets

TRIAZOLE DERIVATIVES, THEIR PREPARATION AND THEIR APPLICATION IN THERAPEUTICS

This application is a U.S. National Phase of International Application No. PCT/EP2009/055213, filed Apr. 29, 2009, designating the U.S. and published in English as WO 2009/133147 on Nov. 5, 2009 which claims the benefit of European Patent Application No. 08155481.8 filed Apr. 30, 2008.

The present invention relates to derivatives of triazole, notably triazole nucleoside, to their preparation, and to their application in therapeutics, and in particular to treat and/or prevent growth of cancer cells, particularly the pancreatic cancer cell lines.

Some triazole nucleoside compounds have already been disclosed in the literature. However their pharmaceutical properties have been few documented. Actually, halo-triazole nucleoside compounds, aryltriazolyl nucleoside compounds and bitriazolyl nucleosides compounds have been described in Wu Q. et al., *Helv. Chim. Acta* 2004, 87, 811-819; Wan J. et al., *Tetrahedron Lett.,* 2006, 47, 6727-6731; Zhu R. et al, *Tetrahedron Lett.,* 2007, 48, 2389-2393; Xia Y. et al., *Org. Biomol. Chem.,* 2007, 5, 1695-701; Li W. et al, *Tetrahedron Lett.,* 2008, 49, 2804-2809 and no specific pharmaceutical activity has been associated thereto.

The inventors have now discovered novel derivatives of triazole of formule (A), notably triazole nucleoside figured out by a compound of formula (I), which possess a powerful anticancer activity, with, at the same time, low toxicity. In particular, they have demonstrated that these novel derivatives are efficient against pancreatic cancer cell lines.

Pancreatic cancer is one of the most lethal human cancers. Almost all patients develop metastases and die. Conventional cancer treatment has little impact on this cancer due to the aggressivity of this cancer and the rapid development of drug resistance. The current first-line treatment is based on gemcitabine, a nucleoside drug. However, it is moderately effective and has only 12% response. Therefore, there is a need to develop new and efficacious candidates for the treatment of pancreatic cancers in particular.

The inventors have herein demonstrated that novel triazole derivatives of formula (A), in particular triazole nucleoside figured out by a compound of formula (I), significantly inhibit the growth of MiaPaCa and Capan-2 cell lines (pancreatic cancer lines) and represent a potent alternative to the reference treatment gemcitabine.

According to a first aspect, the invention relates to a compound of general formula (A):

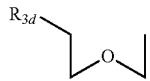
(A)

wherein:
X is

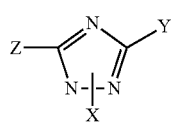
($X_1$)

or

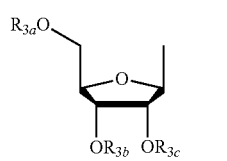
($X_2$)

Y is C(=O)$R_2$ or CN;

Z is $R_1$—C≡C— or

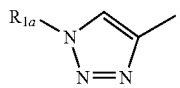

$R_1$ and $R_{1a}$ represents a radical $C_{1-18}$alkyl, $C_{2-18}$alkenyl, $C_{3-10}$cycloalkyl, $C_{3-10}$cycloalkyl-$C_{1-6}$alkylene, $C_{3-10}$cycloalkenyl, $C_{6-20}$aryl, $C_{5-14}$aryl-$C_{1-6}$alkylene, $C_{3-10}$heterocyclyl, $C_{3-10}$heterocyclyl-$C_{1-6}$alkylene, $C_{5-20}$heteroaryl or $C_{5-20}$heteroaryl-$C_{1-6}$alkylene, said radicals being optionally substituted with one or more $R_4$;

$R_2$ represents —$NH_2$, —$NHR_5$, an hydroxyl or a $C_{1-6}$alkoxy group;

$R_{3a}$, $R_{3b}$, $R_{3c}$ and $R_{3d}$ represent independently from each others a hydrogen atom, a $C_{1-18}$alkyl, $C_{2-18}$alkenyl, $C_{6-20}$aryl or —C(O)$R_5$;

$R_4$ represents an halogen atom, an hydroxyl, —$NH_2$, —$NHR_5$, —$NO_2$, —CN, —$CF_3$, —C(O)$R_5$, a radical $C_{1-14}$alkyl, $C_{1-6}$alkoxy, $C_{2-6}$alkenyl, $C_{2-6}$alkynyl, $C_{6-20}$aryl, $C_{5-20}$heteroaryl or $C_{5-14}$aryl-$C_{1-6}$alkylene;

$R_5$ represents $C_{1-18}$alkyl, $C_{2-18}$alkenyl, $C_{2-18}$alkynyl, $C_{5-14}$aryl, $C_{3-10}$heterocyclyl, $C_{5-20}$heteroaryl, $C_{5-14}$aryl-$C_{1-6}$alkylene, $C_{5-14}$aryl-$C_{2-18}$alkenylene, $C_{5-14}$aryl-$C_{2-18}$alkynylene, $C_{5-20}$heteroaryl-$C_{1-6}$alkylene, $C_{5-20}$heteroaryl-$C_{2-18}$alkenylene, $C_{5-20}$heteroaryl-$C_{2-18}$alkynylene, $C_{3-10}$heterocyclyl-$C_{1-6}$alkylene, $C_{3-10}$heterocyclyl-$C_{2-18}$alkenylene or $C_{3-10}$heterocyclyl-$C_{2-18}$ alkynylene;

in the form of a free base or of an addition salt with an acid, as well as in the form of an hydrate or of a solvate.

According to a preferred embodiment, the compound of formula (A) is a compound of formula (I), (I') or (I"):

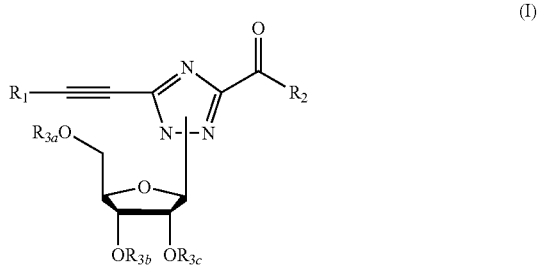
(I)

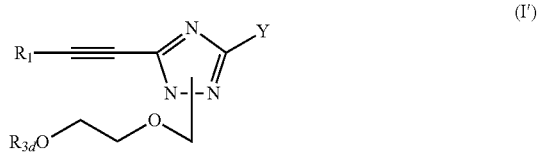
(I')

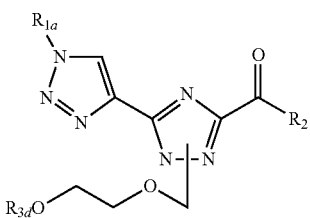
(I")

The compounds of formula (A), notably (I), (I') and (I"), can comprise one or more asymetric carbon atoms. They can therefore exist in the form of enantiomers or diastereoisomers. These enantiomers and diastereoisomers, as well as their mixtures, including racemic mixtures, form part of the invention.

The compounds of formula formula (A), notably (I), (I') and (I"), may comprise an unsaturation site and thus may be in their tautomeric form. The instant invention also extends to the compounds of formula (A), notably (I), (I') and (I"), in their tautomeric form.

The compounds of formula (A), notably (I), (I') and (I"), can be provided in the form of a free base or in the form of addition salts with acids, which also form part of the invention. These salts can be prepared with pharmaceutically acceptable acids, but salts with other acids, useful for example for the purification or for the isolation of the compounds of formula (A), notably (I), (I') and (I"), also form part of the invention.

The compounds of formula (A), notably (I), (I') and (I"), can also exist in the form of a hydrate or of a solvate, i.e. in the form of associations or combinations with one or more water or solvent molecules. Such hydrates and solvates also form part of the invention.

According to the present invention, the terms below have the following meanings.

The terms mentioned herein with prefixes such as for example $C_{1-18}$ or $C_{1-10}$ can also be used with lower numbers of carbon atoms such as $C_{1-8}$ or $C_{1-6}$. If for example the term $C_1$-$C_6$ is used, it means that the corresponding hydrocarbon chain may comprise from 1 to 6 carbon atoms. If for example the term $C_3$-$C_8$ is used, it means that the corresponding hydrocarbon chain or cycle may comprise from 3 to 8 carbon atoms.

The term "halogen atom" corresponds to a fluorine, chlorine, bromine or iodine atom.

The term "alkyl" as used herein refers to a saturated, linear or branched aliphatic group. The following examples may be cited: methyl, ethyl, 1-propyl, 2-propyl, 1-butyl, 2-methyl-1-propyl (also named i-Bu), 2-butyl (also named s-Bu), 2-methyl-2-propyl (also named t-Bu), 1-pentyl (also named n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl. Preferred alkyl according to the invention are methyl, ethyl, 1-propyl, 2-propyl, 1-butyl, 2-methyl-1-propyl (also named i-Bu), 2-butyl (also named s-Bu), 2-methyl-2-propyl (also named t-Bu), 1-pentyl (also named n-pentyl), 2-pentyl, 3-pentyl, 2-methyl-2-butyl, 3-methyl-2-butyl, 3-methyl-1-butyl, 2-methyl-1-butyl.

As used herein and unless otherwise stated, the term "cycloalkyl" means a saturated cyclic alkyl group as defined above. The following examples may be cited: cyclopropyl, methylcyclopropyl, cyclobutyl, methylcyclobutyl, methylcyclopentyl, cyclopentyl, cyclohexyl, methylcyclohexyl, cycloheptyl, methyl cycloheptyl, cyclooctyl and the like, or else a saturated polycyclic alkyl group such as, for examples, norbornyl, fenchyl, trimethyltricycloheptyl or adamantyl. Preferred cycloalkyl according to the invention are cyclopentyl or cyclohexyl.

The term "alkenyl" corresponds to a linear or branched, unsaturated aliphatic group, comprising at least one unsaturation site (usually 1 to 3 and preferably 1), i.e. a carbon-carbon sp2 double bound. The following examples may be cited: ethylene, allyl. The double bond may be in the cis or trans configuration.

The term "cycloalkenyl" corresponds to a cyclic alkenyl group as defined above. The following examples may be cited: cyclopentenyl, 5-hexenyl, 1-hexenyl.

The term "alkynyl" as used herein corresponds to a linear or branched, unsaturated aliphatic group, comprising at least one unsaturation site (usually 1 to 3 and preferably 1), i.e. a carbon-carbon sp3 triple bound. The following examples may be cited: acetylenyl, propargyl.

The term "cycloalkynyl" corresponds to a cyclic alkynyl group as defined above. The following examples may be cited: cyclopentyn-1-yl, cyclohexyn-1-yl.

The term "alkoxy" corresponds to a —O-alkyl group, wherein the alkyl group is as defined above. The following examples may be cited: methoxy, ethoxy, propoxy.

The term "aryl" as used herein means an aromatic mono- or poly-cyclic group. An example of monocyclic group may be phenyl. Examples of polycyclic rings may be naphthalene, anthracene, biphenyl.

The term "heterocyclyl" or "heterocycloalkyl" as used herein refers to a cycloalkyl as described above further comprising at least one heteroatom chosen from nitrogen, oxygen, or sulphur atom. The following examples may be cited: piperidinyl, piperazinyl, morpholinyl, 1,4-dioxanyl, 1,4-dithianyl, homomorpholinyl, 1,3,5-trithianyl, pyrrolidinyl, 2-pyrrolidinyl, tetrahydrofuranyl, tetrahydropyranyl.

The term "heteroaryl" as used herein corresponds to an aromatic, mono- or poly-cyclic group comprising between 5 and 14 carbon atoms and comprising at least one heteroatom such as nitrogen, oxygen or sulphur atom. Examples of such mono- and poly-cyclic heteroaryl group may be: pyridyl, dihydroypyridyl, thiazolyl, thiophenyl, furanyl, azocinyl, pyranyl, pyrrolyl, pyrazolyl, imidazolyl, tetrazolyl, benzofuranyl, thianaphthalenyl, indolyl, indolenyl, quinolinyl, isoquinolinyl, benzimidazolyl, pyrrolinyl, tetrahydroquinolinyl, tetrahydroisoquinolinyl, triazinyl, 6H-1,2,5-thiadiazinyl, 2H,6H-1,5,2-dithiazinyl, thianthrenyl, isobenzofuranyl, chromenyl, xanthenyl, phenoxanthinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, indolinyl, isoindolinyl, oxazolidinyl, benzotriazolyl, benzisoxazolyl, oxindolyl, benzoxazolinyl, benzothienyl, benzothiazolyl, isatinyl, pyridyl, dihydropyridyl, pyrimidinyl, pyrazinyl, s-triazinyl, oxazolyl, thiofuranyl.

The term "aryl-alkylene" as used herein refers to an alkyl radical as defined above, in which one of the hydrogen atoms bonded to a carbon atom, is replaced with an aryl radical as defined above. The following examples may be cited: benzyl, 2-phenylethylen-1-yl, naphthylmethylene, 2-naphthylethylen-1-yl, naphthobenzyl, 2-naphthophenylethylen-1-yl.

This definition applies by analogy to "heteroaryl-alkylene", "cycloalkyl-alkylene" and "heterocycloalkyl-alkylene".

The term "aryl-alkenylene" as used herein refers to an alkenyl radical in which one of the hydrogen atoms bonded to a carbon atom, is replaced with an aryl radical as defined above. The following examples may be cited: 2-phenylethen-1-yl, 2-naphthylethen-1-yl.

This definition applies by analogy to "heteroaryl-alkenylene", "cycloalkyl-alkenylene" and "heterocycloalkyl-alkenylene".

The term "aryl-alkynylene" as used herein refers to an alkynyl radical in which one of the hydrogen atoms bonded to a carbon atom, is replaced with an aryl radical such as defined above. The following examples may be cited: 2-phenylethyn-1-yl, 2-naphthylethyn-1-yl.

This definition applies by analogy to "heteroaryl-alkynylene", "cycloalkyl-alkynylene" and "heterocycloalkyl-alkynylene", Rings as defined above, may be bonded through a carbon atom or an heteroatom, if any.

By way of example, when they are bonded through a carbon atom, they are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example, when they are bonded through an heteroatom such as nitrogen, nitrogen bonded heterocyclic rings are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

Regardless of bond indications, if a substituent is polyvalent (based on its position in the structure referred to), then any and all possible orientations of the substituent are intended.

The "prophylactic and/or therapeutic agent for cancer" as hereunder mentioned may be the compound of formula (I) itself having a prophylactic and/or therapeutic action on cancer or a pharmaceutical agent containing such a substance.

Among the compound of formula (I) according to the invention, a first group of compounds may be defined such that:

$R_1$ represents a radical $C_{6-20}$aryl group and in particular a phenyl group, said radical being substituted with one or more group $R_4$; and $R_4$ represents an halogen atom in particular a fluorine, a —$CF_3$ group, a $C_{1-6}$ alkoxy, in particular a methoxy or else a $C_{1-14}$ alkyl, in particular a methyl or a n-pentyl group, the other groups being as previously defined.

A variant of preferred compound of formula (I), is also represented by a compound of formula (II):

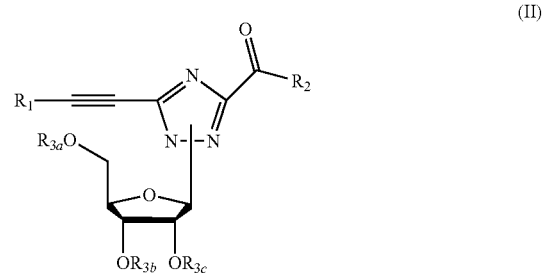

(II)

wherein $R_1$, $R_2$, $R_{3a}$, $R_{3b}$ and $R_{3c}$ are as previously defined for compounds of formula (I).

Among the compound of formula (II) above, a preferred embodiment of the instant invention encompasses a group of compounds of formula (II) wherein:

$R_1$ represents a radical $C_{6-20}$ aryl in particular a phenyl group, said radical being substituted with one or more $R_4$;

$R_4$ represents a —$CF_3$, or a $C_{1-14}$alkyl group in particular a methyl or a n-pentyl;

$R_2$ represents —$NH_2$ or a $C_1$-$C_6$alkoxy group in particular a methoxy;

$R_{3a}$, $R_{3b}$ and $R_{3c}$ represent independently from each others a hydrogen atom or a —C(O)$R_5$; $R_5$ being a $C_{1-6}$alkyl group in particular a methyl.

Among the compounds of this last group, a preferred embodiment of the instant invention encompasses a group of compounds of formula (II) wherein $R_1$ is substituted with one $R_4$ and $R_4$ is in para position on the $C_{6-20}$ aryl radical.

In another preferred embodiment, a group of compounds of formula (II) is defined such as when $R_2$ represents $C_{1-6}$alkoxy in particular a methoxy, and $R_{3a}$, $R_{3b}$ and $R_{3c}$ each represent a —C(O)$R_5$ group, $R_5$ being a $C_{1-6}$ alkyl group and in particular a methyl, then $R_1$ represents a $C_{3-10}$cycloalkenyl in particular a cyclohexen-1-yl radical, optionally substituted with one or more $R_4$, $R_4$ being as defined for the compound of formula (I). Preferably, when $R_1$ represents a $C_{3-10}$cycloalkenyl in particular a cyclohexen-1-yl radical, $R_1$ is unsubstituted.

In another preferred embodiment, a group of compounds of formula (II) is defined such as when $R_2$ represents a —$NH_2$, and $R_{3a}$, $R_{3b}$ and $R_{3c}$ each represent a hydrogen atom, then $R_1$ represents a $C_{3-10}$cycloalkyl in particular a cyclopentyl radical, optionally substituted with one or more $R_4$, $R_4$ being an hydroxyl group.

A variant of preferred compound of formula (I) is represented by a compound of formula (III):

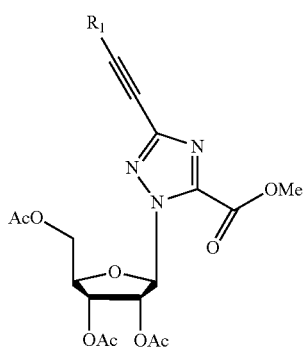

(III)

wherein $R_1$ is optionally substituted with one or more $R_4$, $R_1$ and $R_4$ being as previously defined for the compounds of formula (I), "Ac" representing an acetyl radical —C(O)CH$_3$.

More particularly, in the compound of formula (III), $R_1$ represents a radical $C_{6-20}$aryl and in particular a phenyl group, a radical $C_{3-10}$cycloalkyl in particular a cyclopentyl or a cyclohexyl or a radical $C_{1-18}$alkyl in particular a n-propyl, said radicals being substituted with one or more $R_4$ group, or else $R_1$ represents a $C_{3-10}$cycloalkenyl in particular a cyclohexen-1-yl group optionally substituted with one ore more $R_4$; $R_4$ being as previously defined for the compound of formula (I).

Preferably, in this group, $R_4$ is an halogen atom and in particular a fluorine or a chlorine or an hydroxyl group.

In particular, in the compound of formula (III), when $R_1$ represents a radical $C_{6-20}$ aryl and in particular a phenyl group, which is substituted with one $R_4$, $R_4$ being an halogen atom, then $R_4$ is in para position.

Preferably, in the compound of formula (III), when $R_1$ represents a $C_{3-10}$ cycloalkyl in particular a cyclopentyl or a cyclohexyl, which is substituted with one $R_4$, $R_4$ being an hydroxyl group, then $R_4$ is in position 1 of said cycloalkyl.

In yet another particular variant, preferred compound of formula (I) is represented by a compound of formula (IV):

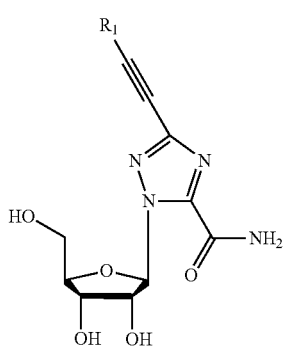

(IV)

wherein $R_1$ is optionally substituted with one or more $R_4$, $R_1$ and $R_4$ being as previously defined for compounds of formula (I).

Among the compounds of this last group, a preferred embodiment of the instant invention encompasses a group of compounds of formula (IV) wherein:

$R_1$ represents a radical $C_{1-18}$alkyl in particular a n-propyl group, a $C_{6-20}$aryl in particular a phenyl group, $C_{3-10}$cycloalkyl in particular a cyclopentyl or a cyclohexyl or a radical $C_{3-10}$cycloalkenyl in particular a cyclohexen-1-yl, said radicals being optionally substituted with one or more $R_4$, $R_4$ being as previously defined for the compounds of formula (I). Preferably, in this case, $R_4$ represents halogen in particular a fluorine or a chlorine atom, a —CF$_3$, a hydroxyl, a $C_{1-14}$alkyl group in particular a n-pentyl or a $C_{1-6}$ alkoxy and preferably a methoxy.

In a preferred embodiment, a group of compounds of formula (IV) is defined such as when $R_1$ represents a $C_{6-20}$ aryl in particular a phenyl group, $R_1$ is substituted with one $R_4$; $R_4$ representing a halogen atom, a —CF$_3$, a $C_{1-14}$alkyl group in particular a n-pentyl or a $C_{1-6}$ alkoxy and in particular a methoxy.

In such a case, $R_4$ is preferably in para position.

Unless otherwise indicated, what is said concerning compound of formula (I) is also valuable for sub-groups of compounds of formulae (II), (III) and (IV).

Among the compound of formula (I) according to the instant invention, the following list of compounds may be cited:

Methyl 5-(4-trifluoromethylphenylethynyl)-1-(2,3,5-tri-O-acetyl-(3-D-ribofuranosyl)-1H-[1,2,4]triazole-3-carboxylate;
Methyl 5-(Cyclohexenylethynyl)-1-(2,3,5-tri-O-acetyl-β-D-ribofuranosyl)-1H-[1,2,4]triazole-3-carboxylate;
5-(4-trifluoromethylphenylethynyl)-1-(2,3,5-tri-Hydroxy-β-D-ribofuranosyl)-1H-[1,2,4]triazole-3-carboxylic acid amide;
3-(4-pentylphenylethynyl)-1-(2,3,5-tri-Hydroxy-β-D-ribofuranosyl)-1H-[1,2,4]triazole-5-carboxylic acid amide;
5-(4-pentylphenylethynyl)-1-(2,3,5-tri-Hydroxy-β-D-ribofuranosyl)-1H-[1,2,4]triazole-3-carboxylic acid amide;
3-(4-fluorophenylethynyl)-1-(2,3,5-tri-Hydroxy-β-D-ribofuranosyl)-1H-[1,2,4]triazole-5-carboxylic acid amide;
3-(3-fluorophenylethynyl)-1-(2,3,5-tri-Hydroxy-β-D-ribofuranosyl)-1H-[1,2,4]triazole-5-carboxylic acid amide;
3-(2-fluorophenylethynyl)-1-(2,3,5-tri-Hydroxy-β-D-ribofuranosyl)-1H-[1,2,4]triazole-5-carboxylic acid amide;
3-(4-trifluoromethylphenylethynyl)-1-(2,3,5-tri-Hydroxy-β-D-ribofuranosyl)-1H-[1,2,4]triazole-5-carboxylic acid amide;
3-(4-Methoxyphenylethynyl)-1-(2,3,5-tri-Hydroxy-β-D-ribofuranosyl)-1H-[1,2,4]triazole-5-carboxylic acid amide;
3-(5-chloropent-1-ynyl)-1-(2,3,5-tri-Hydroxy-β-D-ribofuranosyl)-1H-[1,2,4]triazole-5-carboxylic acid amide;
3-(1-Hydroxycyclohexylethynyl)-1-(2,3,5-tri-Hydroxy-β-D-ribofuranosyl)-1H[1,2,4]triazole-5-carboxylic acid amide;
3-(Cyclohexenylethynyl)-1-(2,3,5-tri-Hydroxy-(3-D-ribofuranosyl)-1H-[1,2,4]triazole-5-carboxylic acid amide.

More preferably, the following list of compounds of formula (I) may be cited:
Methyl 5-(4-trifluoromethylphenylethynyl)-1-(2,3,5-tri-O-acetyl-(3-D-ribofuranosyl)-1H-[1,2,4]triazole-3-carboxylate;
Methyl 5-(Cyclohexenylethynyl)-1-(2,3,5-tri-O-acetyl-(3-D-ribofuranosyl)-1H-[1,2,4]triazole-3-carboxylate;

5-(4-trifluoromethylphenylethynyl)-1-(2,3,5-tri-Hydroxy-β-D-ribofuranosyl)-1H-[1,2,4]triazole-3-carboxylic acid amide;

3-(4-pentylphenylethynyl)-1-(2,3,5-tri-Hydroxy-(3-D-ribofuranosyl)-1H-[1,2,4]triazole-5-carboxylic acid amide.

A variant of preferred compound of formula (I'), is also represented by a compound of formula (II'):

(II')

Among the compound of formula (II') above, a preferred embodiment of the instant invention encompasses a group of compounds of formula (II') wherein:
- $R_1$ represents a radical $C_{6-20}$ aryl in particular a phenyl group, said radical being substituted with one or more $R_4$;
- $R_4$ represents a halogen atom, notably Br, or —$CF_3$;
- Y represents CN or C(=O)$R_2$;
- $R_2$ represents —$NH_2$ or a $C_1$-$C_6$alkoxy group in particular a methoxy;
- $R_{3d}$ represents a hydrogen atom or a —C(O)$R_5$; $R_5$ being a $C_{5-14}$aryl group in particular a phenyl.

More preferably, the following list of compounds of formula (I') may be cited:
- 1-((2-hydroxyethoxy)methyl)-5-(2-(4-bromophenyl)ethynyl)-1H-1,2,4-triazole-3-carboxamide;
- 1-[(2-(benzoyloxy)ethoxy)methyl]-5-(2-(4-trifluoromethylphenyl)ethynyl)-1H-1,2,4-triazole-3-carboxamide; and
- 1-[(2-(benzoyloxy)ethoxy)methyl]-5-(2-(4-trifluoromethylphenyl)ethynyl)-1H-1,2,4-triazole-3-nitrile.

A variant of preferred compound of formula (I"), is also represented by a compound of formula (II"):

(II")

Among the compound of formula (II") above, a preferred embodiment of the instant invention encompasses a group of compounds of formula (II") wherein:
- $R_{1a}$ represents a radical $C_{1-18}$alkyl, or $C_{5-14}$aryl-$C_{1-6}$alkylene;
- $R_2$ represents —$NH_2$ or a $C_1$-$C_6$alkoxy group in particular a methoxy;
- $R_{3d}$ represents a hydrogen atom or a —C(O)$R_5$; $R_5$ being a $C_{1-18}$ alkyl group in particular a methyl.

More preferably, the following list of compounds of formula (I") may be cited:
- 1-((2-hydroxyethoxy)methyl)-5-(1-dodecyl-1H-1,2,3-triazol-4-yl)-1H-1,2,4-triazole-3-carboxamide;
- Methyl 1-((2-acetoxyethoxy)methyl)-5-(1-((pyren-3-yl)methyl)-1H-1,2,3-triazol-4-yl)-1H-1,2,4-triazole-3-carboxylate;
- 1-((2-hydroxyethoxy)methyl)-5-(1-((pyren-3-yl)methyl)-1H-1,2,3-triazol-4-yl)-1H-1,2,4-triazole-3-carboxamide;
- 1-((2-hydroxyethoxy)methyl)-3-(1-((pyren-3-yl)methyl)-1H-1,2,3-triazol-4-yl)-1H-1,2,4-triazole-5-carboxamide;
- 1-((2-hydroxyethoxy)methyl)-5-(1-(naphthalen-1-yl)-1H-1,2,3-triazol-4-yl)-1H-1,2,4-triazole-3-carboxamide; and
- Methyl 1-((2-acetoxyethoxy)methyl)-5-(1-(pyren-3-yl)-1H-1,2,3-triazol-4-yl)-1H-1,2,4-triazole-3-carboxylate.

In accordance with the present invention, the compounds of formula (I) and sub-groups of compounds of formulae (II), (III) and (IV) can be prepared according to the following process.

Starting compounds and reactants, unless otherwise indicated, are commercially available or described in literature, or can be prepared according to methods described in literature or known to one skilled in the art.

The preparation of the compounds of formula (I), as well as compounds of formula (II), (III) and (IV), which figure out sub-groups of compounds of formula (I), may be performed by using Pd-catalyzed Sonogashira coupling reactions under microwave irradiation, such as illustrated in scheme 1.

Scheme 1

(VI)

X = halogen atom (I)

According to scheme 1, the compound of formula (VI), wherein $R_2$, $R_{3a}$, $R_{3b}$ and $R_{1c}$ are as defined for the compound of formula (I) is reacted with a compound of formula (V), wherein $R_1$ is as defined for the compound of formula (I), according to the well know Sonogashira reaction.

More precisely, the compound of formula (V) and the compound of formula (VI) were added in the presence of tetrakis(triphenylphosphine)palladium(0), CuI, triethylamine and were suspended in fresh distilled acetonitrile (MeCN) under argon. The vessel was sealed and irradiated at 100° C. for 25 min, and then cooled to room temperature. The reaction mixture was concentrated under reduced pressure and the crude residue was purified by flash chromatography on silica gel (petroleum ether: ethyl acetate, 2:1). The purified material was dried in vacuo to afford the corresponding product.

According to another embodiment, compounds of formula (I) wherein $R_2$ represents —$NH_2$ and $R_{3a}$, $R_{3b}$ and $R_{3c}$ all represent a hydrogen atom, may be obtained from a compound of formula (I), wherein $R_2$ represents an alkoxy and in particular a methoxy and wherein $R_{3a}$, $R_{3b}$ and $R_{3c}$ represent a —$C(O)R_5$, $R_5$ being in particular an alkyl group, by further dissolution in $NH_3$/MeOH and stirred at room temperature for 2 days. Then the solvent was removed and the residue was washed with $CH_2Cl_2$ to yield the ammonolysis product in pure form.

Compounds according to formula (V) and catalysts may be purchased from Acros or Lancaster.

The preparation of the compound of formula (I') may be performed by using Pd-catalyzed Sonogashira coupling reactions under microwave irradiation as described hereabove, such as illustrated in scheme 2.

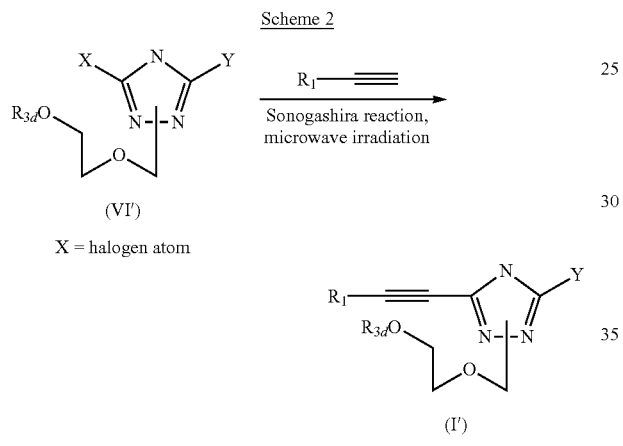

The preparation of the compound of formula (I'') may be performed by using Huisgen cycloaddition reactions, such as illustrated in scheme 3. A suitable procedure has notably been disclosed in Xia Y. et al., *Org. Biomol. Chem.*, 2007, 5, 1695-701 and Li W. et al, *Tetrahedron Lett.*, 2008, 49, 2804-2809.

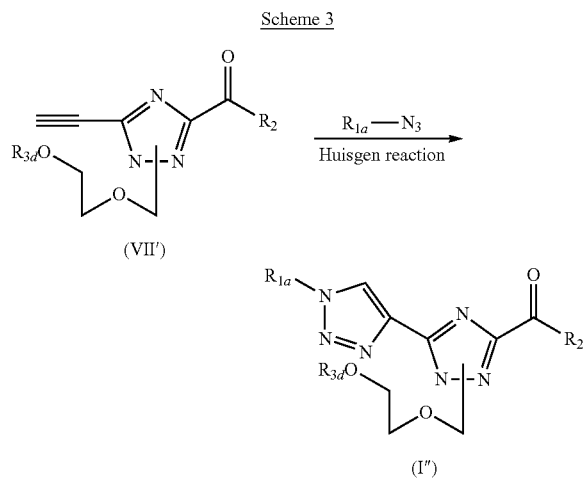

The compounds (VI), (VI') and (VI'') were synthesized according to the procedure described in Wu Q. et al., *Helv. Chim. Acta* 2004, 87, 811-819; Wan J. et al., *Tetrahedron Lett.*, 2006, 47, 6727-6731.

The microwave assisted reactions were performed on an Initiator™ Creator produced by Biotage.

The $^1$H NMR spectra were recorded at 300 or 600 MHz and the $^{13}$C NMR spectra were recorded at 75 or 150 MHz, respectively, on Varian Mercury-VX300 and Varian Inova-600 spectrometers.

The chemical shifts were recorded in parts per million (ppm) with TMS as the internal reference.

FAB and ESI mass spectra were determined using ZAB-HF-3F and Finnigan LCQ Advantage mass spectrometers, respectively.

High resolution mass spectra were obtained by Matrix-assisted laser desorption/ionization mass spectrometry (MALDI-MS) using an IonSpec 4.7 Tesla Fourier Transform Mass Spectrometer.

All the compounds were purified by performing flash chromatography on silica gel (200-300 mesh).

The following examples describe the synthesis of some compounds according to the invention. These examples are not intended to be limitative and only illustrate the present invention. The numbers indicated into brackets in the examples refer to those in Table II.

EXAMPLES

Example 1

Preparation of Methyl 5-(4-trifluoromethylphenylethynyl)-1-(2,3,5-tri-O-acetyl-β-D-ribofuranosyl)-1H-[1,2,4]triazole-3-carboxylate (compound n° 1)

Methyl 5-bromo-[2,3,5-tri-O-acetyl-β-D-ribofuranosyl]-1,2,4-triazole-3-carboxylate (232.0 mg, 0.5 mmol) and 4-trifluoromethylphenylethynyl (0.5 mmol), in presence of tetrakis(triphenylphosphine)palladium(0) (28.9 mg, 0.025 mmol), CuI (9.5 mg, 0.05 mmol) and triethylamine (0.8 mL, 5.7 mmol) were suspended in 4 mL of fresh distilled MeCN under argon. The vessel was sealed and irradiated at 100° C. for 25 min, and then cooled to room temperature. The reaction mixture was concentrated under reduced pressure and the crude residue was purified by flash chromatography on silica gel (petroleum ether: ethyl acetate, 2:1). The purified material was dried in vacuo to afford the corresponding product.

177.1 mg of product was obtained, isolated as a light yellow solid.

$^1$H NMR (300 MHz, CDCl$_3$): δ 7.68-7.76m, 4H, phenyl-H), 6.28 (d, 1H, J=3.6 Hz, H-1') 5.84-5.88 (m, 1H, H-2'), 5.72-5.75 (m, 1H, H-3'), 4.47-4.54 (m, 2H, H-5'), 4.17-4.23 (m, 1H, H-4'), 4.00 (s, 3H, —OCH$_3$), 2.15 (s, 6H, —C(O)CH$_3$), 2.13 (s, 3H, —C(O)CH$_3$);

$^{13}$C NMR (150 MHz, CDCl$_3$): δ 170.8, 169.9, 169.5, 159.4, 155.3, 141.3, 132.8, 132.5q, J$_{CF}$=3.3 H$_{Z1}$123.8, 123.7 (q, J$_{CF}$=270 Hz), 97.0, 89.2, 81.5, 76.0, 74.5, 71.1, 63.0, 53.1, 20.8, 20.7, 20.6;

Maldi-MS: m/z 576.1 [M+Na]$^+$; HRMS: 576.1204

IR: 2233.6 cm$^{-1}$(—C≡C—).

Example 2

Methyl 5-(Cyclohexenylethynyl)-1-(2,3,5-tri-O-acetyl-β-D-ribofuranosyl)-1H-[1,2,4]triazole-3-carboxylate (compound n° 2)

Reaction was performed as described in example 1, except that cyclohexen-1-ylethynyl was used.

91.6 mg of product were obtained, isolated as a colorless oil.

$^1$H NMR (300 MHz, CDCl$_3$): δ6.45-6.47 (m, 1H, alkene-H), 6.18 (d, 1H, J=3.0 Hz, H-1'), 5.80-5.83 (m, 1H, H-2'), 5.70-5.74 (m, 1H, H-3'), 4.41-4.52 (m, 2H, H-5'), 4.15-4.20 (m, 1H, H-4'), 3.97 (s, 3H, —OCH$_3$), 2.18-2.22 (m, 4H, —CH$_2$—), 2.13 (s, 9H, —C(O)CH$_3$), 1.63-1.67 (m, 4H, —CH$_2$—);

$^{13}$C NMR (150 MHz, CDCl$_3$): δ 170.9, 169.6, 19.4, 160.4, 159.7, 154.9, 142.3, 119.0, 101.2, 88.8, 81.3, 81.2, 74.3, 71.8, 71.1, 63.0, 52.9, 28.3, 26.2, 22.1, 21.3, 20.7;

Maldi-MS: m/z 512.2 [M+Na]$^+$;

HRMS: 512.1637;

IR: 2214.5 cm$^{-1}$ (—C≡C—).

Example 3

5-(4-trifluoromethylphenylethynyl)-1-(2,3,5-tri-Hydroxy-β-D-ribofuranosyl)-1H-[1,2,4]triazole-3-carboxylic acid amide (compound n° 3)

Methyl-5-(4-trifluoromethylphenylethynyl)-1-(2,3,5-tri-O-acetyl-β-D-ribofurano-syl)-1H[1,2,4]triazole-3-carboxylate (177.1 mg, 0.32 mmol), prepared according to example 1, was dissolved in 0.2M NH$_3$/MeOH and stirred at room temperature for 2 days. Then the solvent was removed and the residue was washed with CH$_2$Cl$_2$. The product was obtained as a white solid.

114.8 mg of product were obtained, isolated as a white solid.

$^1$H NMR (300 MHz, DMSO-d$_6$): δ 8.09 (br, 1H, —C(O)NH$_2$), 7.89-7.98 (m, 4H, phenyl-H), 7.82 (br, 1H, —C(O)NH$_2$), 6.04 (d, 1H, J=4.5 Hz, H-1'), 5.67 (d, 1H, J=6.0 Hz, —OH), 5.32 (d, 1H, J=6.0 Hz, —OH), 4.83 (t, 1H, J=5.4 Hz, —OH), 4.50-4.55 (m, 1H, H-2'), 4.23-4.28 (m, 1H, H-3'), 3.97-4.02 (m, 1H, H-4'), 3.44-3.61 (m, 2H, H-5');

$^{13}$C NMR (75 MHz, DMSO-d$_6$): δ172.2, 160.3, 157.8, 140.1, 133.7, 131.2 (q, J$_{CF}$=32.9 Hz), 126.7, 124.2, 96.0, 91.3, 86.9, 77.3, 74.9, 71.2, 62.6;

Maldi-MS: m/z 435.1 [M+Na]$^+$;

HRMS: 435.0885;

IR: 2232.8 cm$^{-1}$ (—C≡C—).

Example 4

3-(4-pentylphenylethynyl)-1-(2,3,5-tri-Hydroxy-β-D-ribofuranosyl)-1H-[1,2,4]triazole-5-carboxylic acid amide (compound n° 4)

Methyl 3-(4-pentylphenylethynyl)-1-(2,3,5-tri-O-acetyl-β-D-ribofuranosyl)-1H-[1,2,4]triazole-5-carboxylate (205.6 mg, 0.37 mmol), which was prepared according to the general procedure as previously described in example 1, except that 4-pentylphenylethynyl was used. The obtained product was then dissolved in 0.2M NH$_3$/MeOH and stirred at room temperature for 2 days. Then the solvent was removed and the residue was washed with CH$_2$Cl$_2$.

113.5 mg of product were obtained, isolated as a white solid.

$^1$H NMR (300 MHz, DMSO-d$_6$): δ 8.50 (br s, 1H, —C(O)NH), 8.17 (br s, 1H, —C(O)NH)), 7.55 (d, 1H, J=4.8 Hz, phenyl-H), 7.30 (d, 1H, J=4.8 Hz, phenyl-H), 6.76 (d, 1H, J=3.0 Hz, H-1'), 5.51 (d, 1H, J=5.1 Hz, —OH), 5.19 (d, 1H, J=5.7 Hz, —OH), 5.78 (t, 1H, J=5.4 Hz, —OH), 4.40-4.45 (m, 1H, H-2'), 4.19-4.24 (m, 1H, H-3'), 3.89-3.94 (m, 1H, H-4'), 3.42-3.59 (m, 2H, H-5'), 2.62 (t, 2H, J=7.2 Hz, —CH$_2$—), 1.56-1.61 (m, 2H, —CH$_2$—), 1.25-1.35 (m, 4H, —CH$_2$—), 0.86 (t, 3H, J=7.2 Hz, —CH$_3$);

$^{13}$C NMR (75 MHz, DMSO-d$_6$): δ158.6, 148.9, 146.0, 145.6, 132.5, 129.6, 118.2, 91.4, 90.3, 86.1, 80.2, 74.9, 71.3, 62.7, 35.7, 31.5, 31.0, 22.6, 14.6;

Maldi-MS: m/z 437.2 [M+Na]$^+$;

HRMS: 437.1804;

IR: 2228.0 cm$^{-1}$ (—C≡C—).

Other compounds according to the invention can be prepared by analogy with the method described for the above examples. For examples, compounds n° 5 to 13 (Table I) have been further prepared.

TABLE I

| Compound n° | Chemical name | Physicochemical properties |
|---|---|---|
| 5 | 5-(4-pentylphenylethynyl)-1-(2,3,5-tri-Hydroxy-β-D-ribofuranosyl)-1H-[1,2,4] triazole-3-carboxylic acid amide | $^1$H NMR (300 MHz, DMSO-d$_6$): δ 8.03 (br, 1H, —C(O)NH2), 7.76 (br, 1H, —C(O)NH$_2$), 7.62 (d, 2H, J = 7.8 Hz, phenyl-H), 7.35 (d, 2H, J = 8.1 Hz, phenyl-H), 5.99 (d, 1H, J = 4.2 Hz, H-1'), 5.63 (d, 1H, J = 5.7 Hz, —OH), 5.28 (d, 1H , J = 6.0 Hz, —OH), 4.80 (t, 1H, J = 6.0 Hz, —OH), 4.49-4.54 (m, 1H, H-2'), 4.21-4.26 (m, 1H, H-3'), 3.95-4.00 (m, 1H, H-4'), 3.33-3.62 (m, 2H, H-5'), 2.64 (t, 2H, J =7.5 Hz, —CH$_2$—), 1.54-1.64 (m, 2H, —CH$_2$—), 1.25-1.35 (m, 4H, —CH$_2$—), 0.86 (t, 3H, J = 6.9 Hz, —CH$_3$); $^{13}$C NMR (150 MHz, DMSO-d$_6$): δ 160.4, 157.7, 146.6, 140.8, 132.7, 129.8, 117.1, 98.2, 91.1, 86.9, 74.9, 74.8, 62.7, 35.7, 31.5, 30.9, 22.6, 14.6; Maldi-MS: m/z 437.2 [M + Na]$^+$; HRMS: 437.1798; IR: 2226 cm$^{-1}$ (—C≡C—). |
| 6 | 3-(4-fluorophenylethynyl)-1-(2,3,5-tri-Hydroxy-β-D-ribofuranosyl)-1H-[1,2,4]triazole-5-carboxylic acid amide | $^1$H NMR (300 MHz, DMSO-d$_6$): δ 8.48 (br s, 1H, —C(O)NH), 8.17 (br s, 1H, —C(O)NH), 7.71 (dd, 2H, J1 = 5.7 Hz, J2 = 9.0 Hz, phenyl-H), 7.32 (dd, 2H, J1 = J2 = 5.7 Hz, phenyl-H), 6.74 (d, 1H, J = 3.0 Hz, H-1'), 5.51 (d, 1H, J = 5.1 Hz, —OH), 5.19 (d, 1H, J =5.7 Hz, —OH), 4.77 (t, 1H, J = 5.4 Hz, —OH), 4.38-4.42 (m, 1H, H-2'), 4.17-4.22 (m, 1H, H-3'), 3.86-3.91 (m, 1H, H-4'), 3.38-3.57 (m, 2H, H-5'); $^{13}$C NMR (150 MHz, DMSO-d$_6$): δ 163.5 (d, J$_{CF}$ = 255 Hz), 158.5, 149.0, 145.8, 135.1 (d, J$_{CF}$ = 8.55 Hz), 117.3, 117.1 (d, J$_{CF}$ = 21.3 Hz), 91.4, 89.1, 86.1, 80.4, 74.9, 71.3, 62.7; |

TABLE I-continued

| Compound n° | Chemical name | Physicochemical properties |
|---|---|---|
| 7 | 3-(3-fluorophenylethynyl)-1-(2,3,5-tri-Hydroxy-β-D-ribofuranosyl)-1H-[1,2,4]triazole-5-carboxylic acid amide | Maldi-MS: m/z 385.1 [M + Na]$^+$; HRMS: 385.0923; IR: 2233.1 cm$^{-1}$ (—C≡C—). $^1$H NMR (300 MHz, DMSO-d$_6$): δ 8.51 (br s, 1H, —C(O)NH), 8.19 (br s, 1H, —C(O)NH), 7.51-7.57 (m, 3H, phenyl-H), 7.39-7.42 (m, 1H, phenyl-H), 6.76 (d, 1H, J = 3.0 Hz, H-1'), 5.52 (d, 1H, J = 5.1 Hz, —OH), 5.20 (d, 1H, J = 6.0 Hz, —OH), 4.78 (t, 1H, J = 6.0 Hz, —OH), 4.38-4.42 (m, 1H, H-2'), 4.18-4.24 (m, 1H, H-3'), 4.17-4.22 (m, 1H, H-4'), 3.38-3.58 (m, 2H, H-5'); $^{13}$C NMR (150 MHz, DMSO-d$_6$): δ 162.6 (d, J$_{CF}$ = 255 Hz), 158.5, 149.1, 145.5, 131.8, 129.0, 122.8, 119.1 (d, J$_{CF}$ = 22.7 Hz), 118.1 (d, J$_{CF}$ = 20.4 Hz), 91.5, 88.6, 86.2, 81.5, 74.9, 71.3, 62.7; Maldi-MS: m/z 385.1 [M + Na]$^+$; HRMS: 385.0920; IR: 2235.5 cm$^{-1}$ (—C≡C—). |
| 8 | 3-(2-fluorophenylethynyl)-1-(2,3,5-tri-Hydroxy-β-D-ribofuranosyl)-1H-[1,2,4]triazole-5-carboxylic acid amide | $^1$H NMR (300 MHz, DMSO-d$_6$): δ 8.53 (br s, 1H, —C(O)NH), 8.19 (br s, 1H, —C(O)NH), 7.73 (dd, 1H, J$_1$ = J$_2$ = 7.2 Hz, phenyl-H), 7.59 (dd, 1H, J$_1$ = 7.2 Hz, J$_2$ = 13.8 Hz, phenyl-H), 7.41 (dd, 1H, J1 = J2 = 9.0 Hz, phenyl-H), 7.32 (dd, 1H, J$_1$ = J$_2$ = 8.1 Hz, phenyl-H), 6.77 (d, 1H, J = 3.6 Hz, H-1'), 5.53 (d, 1H, J = 6.0 Hz, —OH), 5.20 (d, 1H, J = 5.7 Hz), 4.78 (t, 1H, J = 5.7 Hz, —OH), 4.41-4.45 (m, 1H, H-2'), 4.19-4.24 (m, 1H, H-3'), 3.88-3.93 (m, 1H, H-4'), 3.39-3.57 (m, 2H, H-5'); $^{13}$C NMR (150 MHz, DMSO-d$_6$): δ 162.4 (d, J$_{CF}$ = 255 Hz)158.5, 149.1, 145.5, 134.5, 133.8, 125.8, 116.7 (d, J$_{CF}$ = 19.4 Hz), 109.4, 91.5, 86.2, 85.5, 83.5, 74.9, 71.4, 62.7; Maldi-MS: m/z 385.1 [M + Na]$^+$; HRMS: 385.0917; IR: 2235.2 cm$^{-1}$ (—C≡C—). |
| 9 | 3-(4-trifluoromethyl-phenyl-ethynyl)-1-(2,3,5-tri-Hydroxy-β-D-ribofuranosyl)-1H-[1,2,4]triazole-5-carboxylic acid amide | $^1$H NMR (300 MHz, DMSO-d$_6$): δ 8.66 (br s, 1H, —C(O)NH), 8.34 (br s, 1H, —C(O)NH), 7.96-8.04 (m, 4H, phenyl-H), 6.90 (d, 1H, J = 3.6 Hz, H-1'), 5.69 (d, 1H, J = 6.0 Hz, —OH), 5.36 (d, 1H, J = 5.7 Hz, —OH), 4.94 (t, 1H, J = 6.0 Hz, —OH), 4.54-4.57 (m, 1H, H-2'), 4.33-4.36 (m, 1H, H-3'), 4.02-4.06 (m, 1H, H-4'), 3.56-3.86 (m, 2H, H-5'); $^{13}$C NMR (150 MHz, DMSO-d$_6$): δ 158.5, 149.1, 145.4, 133.4, 130.5 (t, J$_{CF}$ = 31.1 Hz), 126.5, 125.2, 122.7, 91.5, 88.5, 86.2, 82.8, 74.9, 71.3, 62.7; Maldi-MS: m/z 435.1 [M + Na]$^+$; HRMS: 435.0892; IR: 2237.0 cm$^{-1}$ (—C≡C—). |
| 10 | 3-(4-Methoxyphenyl-ethynyl)-1-(2,3,5-tri-Hydroxy-β-D-ribofuranosyl)-1H-[1,2,4]triazole-5-carboxylic acid amide | $^1$H NMR (300 MHz, DMSO-d$_6$): δ 8.44 (br s, 1H, —C(O)NH), 8.12 (br s, 1H, —C(O)NH), 7.57 (d, 2H, J = 8.7 Hz, phenyl-H), 7.01 (d, 2H, J = 8.7 Hz, phenyl-H), 6.74 (d, 1H, J = 2.7 Hz, H-1'), 5.47 (d, 1H, J = 5.7 Hz, —OH), 5.15 (d, 1H, J = 6.3 Hz, —OH), 4.74 (t, 1H, J = 5.7 Hz, —OH), 4.37-4.42 (m, 1H, H-2'), 4.19-4.22 (m, 1H, H-3'), 3.88-3.91 (m, 1H, H-4'), 3.80 (s, 3H, —OCH$_3$), 3.32-3.57 (m, 2H, H-5'); $^{13}$C NMR (150 MHz, DMSO-d$_6$): δ 163.3, 160.9, 150.7, 148.4, 136.4, 117.5, 114.5, 93.5, 93.1, 87.8, 81.2, 76.9, 73.2, 64.6, 58.1; Maldi-MS: m/z 397.1 [M + Na]$^+$; HRMS: 397.1130; IR: 2233.5 cm$^{-1}$ (—C≡C—). |
| 11 | 3-(5-chloropent-1-ynyl)-1-(2,3,5-tri-Hydroxy-β-D-ribofuranosyl)-1H-[1,2,4]triazole-5-carboxylic acid amide | $^1$H NMR (300 MHz, DMSO-d$_6$): δ 8.41 (br s, 1H, —C(O)NH), 8.12 (br s, 1H, —C(O)NH), 6.71 (d, 1H, J = 3.3 Hz, H-1'), 5.47 (d, 1H, J = 5.4 Hz, —OH), 5.16 (d, 1H, J = 5.7 Hz, —OH), 4.75 (t, 1H, J = 5.7 Hz, —OH), 4.34-4.38 (m, 1H, H-2'), 4.15-4.19 (m, 1H, H-2'), 3.86-3.90 (m, 1H, H-3'), 7.74 (t, J = 6.3 Hz, 2H, —CH$_2$—), 3.40-3.60 (m, 2H, H-5'), 2.63 (t, 2H, J = 6.9 Hz, —CH$_2$—), 1.96-2.01 (m, 2H, —CH$_2$—); $^{13}$C NMR (150 MHz, DMSO-d$_6$): δ 158.6, 148.6, 146.0, 91.2, 91.2, 86.0, 74.8, 72.8, 71.3, 62.7, 44.7, 31.0, 16.5; Maldi-MS: m/z 367.1 [M + Na]$^+$; HRMS: 367.0782; IR: 2251.4 cm$^{-1}$(—C≡C—). |
| 12 | 3-(1-Hydroxycyclohexyl-ethynyl)-1-(2,3,5-tri-Hydroxy-β-D-ribofuranosyl)-1H-[1,2,4]triazole-5-carboxylic acid amide | $^1$H NMR (300 MHz, DMSO-d$_6$): δ 8.55 (br s, 1H, —C(O)NH), 8.23 (br s, 1H, —C(O)NH), 6.82 (d, 1H, J = 3.6 Hz, H-1'), 5.82 (s, 1H, —OH), 5.61 (d, 1H, J = 5.1 Hz, —OH), 5.31 (d, 1H, J = 5.1 Hz, —OH), 4.89 (t, 1H, J = 5.1 Hz, —OH), 4.46-4.49 (m, 1H, H-2'), 4.25-4.31 (m, 1H, H-2'), 3.96-4.01 (m, 1H, H-3'), 3.46-3.67 (m, H-5'), 1.93-2.01 (m, 2H, cyclohexanyl-H), 1.67-1.82 (m, 2H, cyclohexanyl-H), 1.53-1.63 (m, 1H, cyclohexanyl-H); $^{13}$C NMR (150 MHz, DMSO-d$_6$): δ 158.6, 148.7, 145.9, 96.2, 91.2, 86.0, 74.8, 67.5, 62.7, 42.2, 25.3, 23.7, 23.6; Maldi-MS: m/z 389.1 [M + Na]$^+$; HRMS: 389.1439; IR: 2249.6 cm$^{-1}$ (—C≡C—). |
| 13 | 3-(Cyclohexenylethynyl)-1-(2,3,5-tri-Hydroxy-β-D-ribofuranosyl)-1H-[1,2,4]triazole-5-carboxylic acid amide | $^1$H NMR (300 MHz, DMSO-d$_6$): δ 8.45 (br s, 1H, —C(O)NH), 8.12 (br s, 1H, —C(O)NH), 6.22 (d, 1H, J = 3.3 Hz, H-1'), 5.37 (s, 1H, —C═CH), 5.48 (d, 1H, J = 5.4 Hz, —OH), 5.17 (d, 1H, J = 5.7 Hz, —OH), 4.76 (t, 1H, J = 5.7 Hz, —OH), 4.16-4.19 (m, 1H, H-2'), 4.25-4.31 (m, 1H, H-2'), 3.86-3.90 (m, 1H, H-3'), 3.40-3.60 (m, 2H, H-5'), 2.14-2.17 (m, 4H, Cyclohexenylethynyl-H), 1.56-1.61 (Cyclohexenylethynyl-H); $^{13}$C NMR (150 MHz, DMSO-d$_6$): δ 158.6, 148.8, 146.2, 139.3, 119.3, 92.1, 91.3, 86.0, 78.3, 74.8, 71.3, 62.7, 28.7, 26.0, 22.3, 21.4; Maldi-MS: m/z 371.1 [M + Na]$^+$; HRMS: 371.1335; IR: 2220.0 cm$^{-1}$ (—C≡C—). |

Example 5

Preparation of 1-((2-hydroxyethoxy)methyl)-5-(2-(4-bromophenyl)ethynyl)-1H-1,2,4-triazole-3-carboxamide (compound n° 14)

The 4-bromomethylphenylethynyl (34.1 mg, 1.2 eq), tetrakis (triphenylphosphine) palladium(0) (12.3 mg, 0.1 eq), CuI (1.7 mg, 0.05 eq), $Li_2CO_3$ (31.2 mg, 2 eq) and 5-bromo-1-[(2-hydroxyethoxy)methyl]-1,2,4-triazole-3-carboxamide (40.3 mg) were suspended in 2.8 mL of dioxane/$H_2O$ (3/1) under argon. The vessel was sealed and subjected to microwave irradiation at 100° C. for 25 min, and then cooled to room temperature. The reaction mixture was concentrated under reduced pressure and the crude residue was purified by flash chromatography on silica gel ($CH_2Cl_2/CH_3OH$, 20:1). The purified material was dried in vacuo to afford the corresponding product.

26.6 mg of product was obtained, isolated as a light yellow solid.

$^1$HNMR (300 MHz, $CDCl_3$): δ 7.58 (d, 2H, ArH), 7.48 (d, 2H, ArH), 7.03 (—C(O)NH), 5.75 (m, 3H, H-1'+—C(O)NH), 3.80-3.77 (m, 4H, —$CH_2$—$CH_2$), 1.91 (t, J=5.7 Hz, —OH).

HRMS: m/z calcd. for $C_{14}H_{14}N_4BrO_3^+$ 365.0244, Found 365.0258.

IR (KBr): —C≡C— (2233 $cm^{-1}$).

Example 6

1-[(2-(benzoyloxy)ethoxy)methyl]-5-(2-(4-trifluoromethylphenyl)ethynyl)-1H-1,2,4-triazole-3-carboxamide (compound n° 15)

1-((2-hydroxyethoxy)methyl)-5-(2-(4-trifluoromethylphenyl)ethynyl)-1H-1,2,4-triazole-3 carboxamide (35.8 mg), $Bz_2O$ (27.2 mg, 1.2 eq) and DMAP (12.5 mg, 0.1 eq) were dissolved in $CH_2Cl_2$ and stirred at room temperature for 24 h, at which point TLC analysis indicated complete consumption of starting material. The solvent in reaction mixture was evaporated and the residue was purified by flash chromatography on silica gel ($CH_2Cl_2/CH_3OH$, 30:1). The purified material was dried in vacuo to afford the corresponding product.

37.6 mg of product were obtained, isolated as a white powder.

$^1$H NMR (300 MHz, $CDCl_3$): δ 8.00-7.98 (d, 2H, ArH), 7.68-7.63 (dd, 4H, J=8.7 Hz), 7.55-7.53 (m, 1H, ArH), 7.43-7.38 (m, 2H, ArH), 7.03 (—C(O)NH), 5.93 (—C(O)NH), 5.78 (s, 2H, H-1'), 4.51-4.48 (t, 2H, J=4.4 Hz, H-2'), 4.05-4.03 (t, 2H, J=4.2, H-3').

$^{13}$CNMR (150 MHz, $CDCl_3$): δ 166.5, 160.3, 156.5, 140.7, 133.4, 132.8, 132.5, 132.3, 129.9, 128.6, 125.9, 123.8, 123.7 ($J_1$=271.6 Hz), 96.8, 78.7, 76.2, 68.6, 63.3.

HRMS: m/z calcd. for $C_{22}H_{18}F_3N_4O_4^+$ 459.1275, Found 459.1276.

IR (KBr): —C≡C— (2233 $cm^-$)

Example 7

1-[(2-(benzoyloxy)ethoxy)methyl]-5-(2-(4-trifluoromethylphenyl)ethynyl)-1H-1,2,4-triazole-3-nitrile (compound n° 16)

The solution of compound n° 15 (37.4 mg) in $POCl_3$ (5 mL) was heated at 70° C. for 1 h and then concentrated. The residue was dissolved in EtOAc and then washed with aqueous saturated $NaHCO_3$, water and brine. The organic phase was dried over $Na_2SO_4$ and then concentrated. The crude product was purified by flash chromatography on silica gel (Petroleum ether/EtOAc, 6:1). The purified material was dried in vacuo to afford the corresponding product.

15.4 mg of product were obtained, isolated as a white powder.

$^1$H NMR (300 MHz, $CDCl_3$): δ 8.00-7.98 (d, 2H, ArH), 7.72-7.65 (dd, 4H, J=8.8 Hz), 7.60-7.55 (s, 1H, ArH), 7.48-7.40 (d, 2H, ArH), 5.76 (s, 2H, H-1'), 4.51 (t, 2H, J=4.5 Hz, H-2'), 4.02 (t, 2H, J=5.1, H-3).

$^{13}$CNMR (150 MHz, $CDCl_3$): δ 166.5, 141.5, 139.8, 133.6, 132.9, 132.8, 132.6, 129.8, 129.7, 128.7, 125.9, 123.8 ($J_1$=270.6 Hz), 122.7, 111.3, 97.7, 78.9, 75.3, 68.9, 63.2.

Maldi-MS: m/z 463.1.

IR (KBr): —C≡C— (2233 $cm^{-1}$), —CN (2258 $cm^{-1}$).

Example 8

1-((2-hydroxyethoxy)methyl-5-(1-dodecyl-1H-1,2,3-triazol-4-yl)-1H-1,2,4-triazole-3-carboxamide (compound n° 17)

The methyl 1-((2-acetoxyethoxy)methyl)-5-ethynyl-1H-1,2,4-triazole-3-carboxylate (26.6 mg, 0.1 mmol), $CuSO_4.5H_2O$ (1.3 mg, 0.05 eq) and sodium ascorbate (10.2 mg, 0.5 eq) dissolved in a mixed solvent system (THF/$H_2O$=1/3, 4 ml) under Ar protection. The azide (28.0 mg, 1.2 eq) was added. The yellow mixture was stirred at 45° C., at which point TLC analysis indicated complete cosumption of alkyne. The solvent in the reaction mixture was evaporated and the residue was puried by flash chromatography on silica gel (Petroleum ether/EtOAc, 1:1). The product was dried in vacuo to afford product n°17-1 (39.3 mg).

45.6 mg of compound n° 17-1 was dissolved in 10 ml saturated $NH_3$/MeOH and stirred at room temperature for 1 day. Then the solvent was removed and the residue was purified by flash chromatography on silica gel ($CH_2Cl_2/CH_3OH$, 20:1). The purified material was dried in vacuo to afford the corresponding product.

35.6 mg of product were obtained, isolated as a white powder.

$^1$H NMR (300 MHz, DMSO-$d_6$): δ 8.81 (s, 1H, alkene-H), 7.86 (—C(O)NH), 7.69 (—C(O)NH), 6.01 (s, 2H, H-1'), 4.68 (t, 1H, J=5.4 Hz, —OH), 4.48 (t, 2H, J=6.9 Hz, —$CH_2$), 3.59 (t, 2H, J=5.1 Hz, H-2'), 3.48-3.43 (m, 2H, H-3'), 1.88 (m, 2H, —$CH_2$), 1.23 (s, 16H, —($CH_2$)8), 0.85 (t, 3H, J=6.3 Hz, —$CH_3$).

$^{13}$CNMR (150 MHz, DMSO-$d_6$): δ 160.9, 157.2, 148.4, 136.4, 126.9, 79.2, 71.8, 60.5, 50.5, 32.0, 30.2, 29.7, 29.5, 29.4, 29.0, 26.4, 22.8, 14.6.

HRMS: m/z calcd. for $C_{23}H_{39}N_6O_5^+$ 479.2976, Found 479.2971.

Example 9

Methyl 1-((2-acetoxyethoxy)methyl)-5-(1-((pyren-3-yl)methyl)-1H-1,2,3-triazol-4-yl)-1H-1,2,4-triazole-3-carboxylate (compound n° 18)

The methyl 1-((2-acetoxyethoxy)methyl)-5-ethynyl-1H-1,2,4-triazole-3-carboxylate (26.1 mg, 0.1 mmol), $CuSO_4.5H_2O$ (1.2 mg, 0.05 eq) and sodium ascorbate (10.3 mg, 0.5 eq) dissolved in a mixed solvent system (THF/$H_2O$=3/1, 4 ml) under Ar protection. The azide (30 mg, 1.2 eq) was added. The yellow mixture was stirred at 45° C., at which point TLC analysis indicated complete cosumption of alkyne. The solvent in the reaction mixture was evaporated and the residue was puried by flash chromatography on silica gel (Petroleum ether/EtOAc, 1:1). The product was dried in vacuo to afford the corresponding product.

52.2 mg of product were obtained, isolated as a white powder.

$^1$HNMR (300 MHz, CDCl$_3$): δ 8.27-8.03 (m, 10H, =C—H+ArH), 6.33 (s, 2H, H-1'), 6.24 (s, 2H, —CH$_2$), 4.15 (t, 2H, J=4.4 Hz, H-2'), 3.92 (s, 3H, —OCH$_3$), 3.87 (t, 2H, J=4.4 Hz, H-3'), 1.98 (s, 3H, —C(O)CH$_3$).

$^{13}$CNMR (150 MHz, CDCl$_3$): δ 171.0, 160.1, 154.2, 148.5, 137.1, 132.8, 131.3, 130.7, 129.65, 129.59, 128.8, 128.2, 127.4, 126.7, 126.4, 126.2, 125.6, 125.5, 125.4, 125.2, 124.6, 121.7, 79.4, 68.1, 63.1, 53.0, 21.0.

HRMS: m/z calcd. for C$_{28}$H$_{24}$N$_6$NaO$_5$$^+$ 547.17, Found 547.1693.

Example 10

1-((2-hydroxyethoxy)methyl)-5-(1-((pyren-3-yl)methyl)-1H-1,2,3-triazol-4-yl)-1H-1,2,4-triazole-3-carboxamide (compound n° 19)

52.2 mg of compound n° 18 was dissolved in 10 ml saturated NH$_3$/MeOH and stirred at room temperature for 1 day. Then the solvent was removed and the residue was purified by flash chromatography on silica gel (CH$_2$Cl$_2$/CH$_3$OH, 20:1). The purified material was dried in vacuo to afford the corresponding product.

36.9 mg of product were obtained, isolated as a white powder.

$^1$H NMR (300 MHz, DMSO-d6): δ 8.89 (s, 1H, =C—H), 8.62-8.59 (d, 1H, ArH), 8.37-8.13 (m, 8H, ArH), 7.86 (—C(O)NH), 7.66 (—C(O)NH), 6.55 (s, 2H, H-1'), 5.99 (s, 2H, —CH$_2$), 4.67 (t, 1H, J=5.7 Hz, —OH), 3.56 (t, 2H, J=5.1 Hz, H-2'), 3.43 (t, 2H, J=5.1 Hz, H-3').

$^{13}$CNMR (150 MHz, DMSO-d$_6$): δ 160.8, 157.1, 148.0, 136.6, 131.9, 131.4, 130.8, 129.2, 129.1, 128.7, 128.6, 128.0, 127.3, 127.1, 126.5, 126.4, 125.8, 124.7, 124.4, 123.4, 79.2, 71.7, 60.4, 51.9.

HRMS: m/z calcd. for C$_{25}$H$_{21}$N$_7$NaO$_3$$^+$ 490.1604, Found 490.1596.

Example 11

1-((2-hydroxyethoxy)methyl)-3-(1-((pyren-3-yl)methyl)-1H-1,2,3-triazol-4-yl)-1H-1,2,4-triazole-5-carboxamide (compound n° 20)

Reaction was performed as described in examples 5 and 6, except methyl 1-((2-acetoxyethoxy)methyl)-3-ethynyl-1H-1,2,4-triazole-5-carboxylate was used.

77.7 mg of product were obtained, isolated as white solid.

$^1$HNMR (300 MHz, DMSO-d$_6$): δ 8.64 (s, 1H, =C—H), 8.60 (d, 2H, ArH), 8.37-8.33 (m, 6H, ArH), 8.27-8.19 (m, 2H, ArH), 8.13-8.08 (m, 3H, ArH+-C(O)NH$_2$), 6.49 (s, 2H, H-1'), 5.92 (s, 2H, —CH$_2$), 4.68 (t, 1H, J=5.7 Hz, —OH), 3.53 (t, 2H, J=4.8 Hz, H-2'), 3.42 (t, 2H, J=3.9 Hz, H-3').

HRMS: m/z calcd. for C$_{25}$H$_{21}$N$_7$NaO$_3$$^+$ 490.1598, Found 490.1609.

Example 12

1-((2-hydroxyethoxy)methyl)-5-(1-(naphthalen-1-yl)-1H-1,2,3-triazol-4-yl)-1H-1,2,4-triazole-3-carboxamide (compound n° 21)

Reaction was performed as described in examples 5 and 6, except 1-azidonaphthalene was used.

32 mg of product were obtained, isolated as white solid.

$^1$HNMR (300 MHz, DMSO-d$_6$): δ 9.34 (s, 1H, =C—H), 8.29-8.26 (d, 1H, ArH), 8.19-8.16 (d, 1H, ArH), 7.96 (—C(O)NH), 7.89-7.87 (d, 1H, ArH), 7.79-7.64 (m, 4H, —C(O)NH+ArH), 6.11 (s, 2H, H-1'), 4.74 (t, 1H, J=5.7 Hz, —OH), 3.67 (t, 2H, J=5.1 Hz, H-2'), 3.52 (t, 2H, J=5.4 Hz, H-3').

$^{13}$CNMR (150 MHz, DMSO-d$_6$): δ 161.1, 156.7, 148.1, 136.5, 134.3, 133.0, 131.6, 129.5, 129.1, 129.0, 128.4, 128.1, 126.2, 125.0, 122.3, 79.3, 71.6, 60.3.

HRMS: m/z calcd. for C$_{18}$H$_{17}$N$_7$NaO$_3$$^+$ 402.1285, Found 402.1293

Example 13

Methyl 1-((2-acetoxyethoxy)methyl)-5-(1-(pyren-3-yl)-1H-1,2,3-triazol-4-yl)-1H-1,2,4-triazole-3-carboxylate (compound n° 22)

Reaction was performed as described in examples 5, except 1-azidopyrene was used.

41.7 mg of product were obtained, isolated as white solid.

$^1$HNMR (300 MHz, CDCl$_3$): δ 8.88 (s, 1H, =C—H), 8.35-7.89 (m, 8H, ArH), 7.90 (d, 1H, ArH), 6.43 (s, 2H, H-1'), 4.27 (t, 2H, J=5.2 Hz, H-2'), 4.08 (s, 3H, OMe), 4.04 (t, 2H, J=5.1 Hz, H-3'), 2.08 (s, 3H, OAc).

$^{13}$CNMR (600 MHz, CDCl$_3$): δ 171.2, 160.3, 154.5, 148.6, 137.2, 132.9, 131.2, 130.7, 130.4, 129.6, 129.4, 128.4, 127.2, 127.1, 127.0, 126.6, 126.0, 125.2, 125.1, 124.2, 123.3, 120.6, 79.7, 68.3, 63.3, 53.4, 21.2

The compounds of the invention underwent pharmacological studies which demonstrated their anticancer properties and their value as therapeutically active substances.

In the following examples, it is referred to the following figures.

Figure 1:
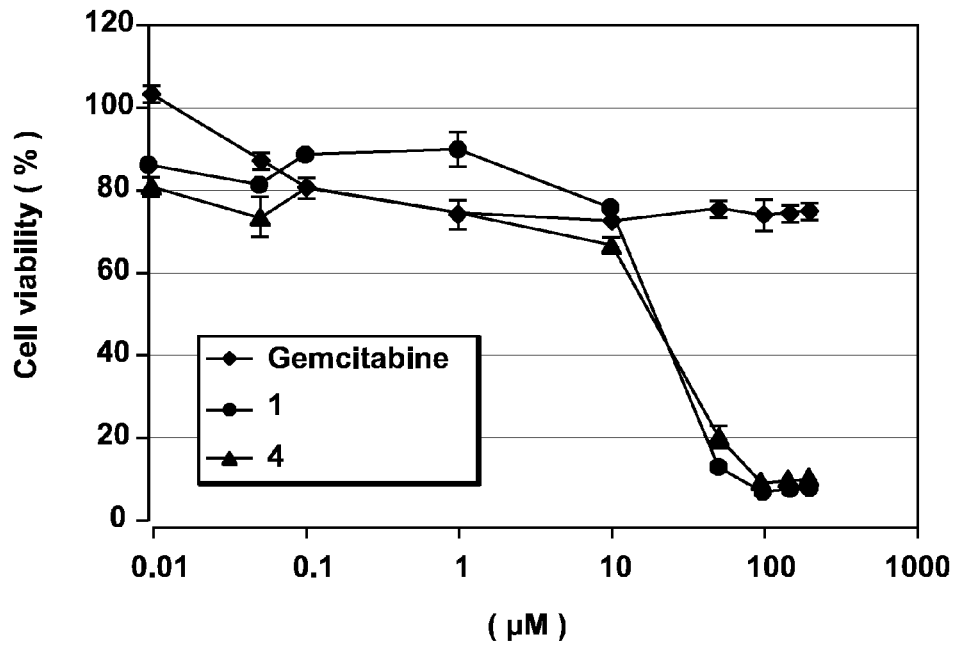
FIG. 1 illustrates the results of the dose-dependency study on MiaPaCa cells for some compounds according to the invention, compounds n° 1 and 4, compared to gemcitabine.

A. PRE-DETERMINATION AND INVESTIGATION OF INHIBITION EFFECT OF THE COMPOUNDS OF THE INVENTION ON CELL SURVIVAL

This test was performed in order to investigate compounds, which exhibit similar potency as gemcitabine and more preferably, which are more potent than gemcitabine.

Pancreactic cancer cell lines, MiaPaCa cells were cultured in DMEM medium (Gibco) supplemented with 10% fetal bovine serum (FBS). Cells were seeded at a densitiy of 15,000 cells per well in 96 well View Plate™ (Packard) in 250 µl of medium containing the same components as described above.

For Capan-2 cell lines, the cells were cultured in RPMI 1640 medium supplemented with 10% FBS and 1% glutamine. Cells were seeded at a densitiy of 20,000 cells per well in 96 well View Plate™ (Packard) in 250 µl of medium containing the same components as described above.

Cells were allowed to adhere and proliferate for 24 hr. At that time, culture medium was removed and serial dilutions from 10 nM to 200 µM of the test compounds were added in culture medium. Gemcitabine and no treatment were included as positive and negative controls. Plates were further incubated at 37° C. and 5% $CO_2$ for 48 hours. The number of viable cells remaining after the appropriate treatment was determined by Colorimetric Assay (3-(4,5-dimethylthiazol-2-yl)-2,5-diphenyl tetrazolium bromide, MTT).

Inhibition of MiaPaCa and Capan-2 cells were tested at different doses of compounds of the invention: 50 µM, 100 µM and 200 µM.

Compounds of the instant invention exhibit a significant inhibition activity on cancer cells. Actually, compounds according to the present invention are particularly potent on chemo-resistant cancer cell line (MiaPaCa) and/or on chemo-sensitive cancer cell line (Capan-2).

Inhibition effect of compounds according to the present invention on sensitive and/or resistant-drug cancer cells is of at least 10%. Preferably, it is between 10% and 90%, more preferably between 15% and 80%, and more preferably between 20% and 65%. Actually, the most potent compounds of the invention exhibit more than 50% of inhibition at 50 µM.

Results are provided for some compounds of the invention at the lowest dose, i.e. at 50 µM in chemo-resistant and fast-growing MiaPaCa and chemo-sensitive and slow growing Capan-2 cell lines. The results, compared to the reference drug gemcitabine used at the same concentration are provided in Table II and Table III.

TABLE II

| Compounds | Inhibition effect on MiaPaCa at 50 µM (%) | Inhibition effect on Capan-2 at 50 µM (%) |
|---|---|---|
| Gemcitabine | 29.3 | 61.7 |
| 1 | 59.1 | 62.9 |
| 2 | 21.3 | 57.6 |
| 3 | 5.5 | 53.8 |
| 4 | 52.5 | 25.2 |

As demonstrated in Table II, compounds according to the instant invention exhibit similar potency as gemcitabine and preferably are more potent than gemcitabine.

More precisely, according to Table II, compounds of the invention are either active on MiaCaPa and/or Capan-2 cell lines. For example:

- compound n° 1 exhibits more than 50% of inhibition on both cell types.
- compound n° 2 is more potent on chemo-sensitive and slow-growing Capan-2 cells, but also demonstrates a significant inhibition activity on chemo-resistant and fast-growing MiaPaCa cells,
- compound n° 3 is more potent on chemo-sensitive and slow-growing Capan-2 cells compare to the chemo-resistant and fast-growing cells.
- compound n° 4 is more potent on chemo-resistant and fast-growing MiaPaCa cells but also exhibits a quite good inhibition activity on chemo-sensitive and slow-growing Capan-2 cells.

TABLE III

| Compounds | Inhibition effect on MiaPaCa-2 at 50 µM (%) | Inhibition effect on Capan-2 at 50 µM (%) |
|---|---|---|
| Gemcitabine | 29.3 | 61.7 |
| 14 | 68.7 | 51.5 |
| 15 | 58.2 | 61.7 |
| 16 | 72.8 | 84.5 |
| 17 | 43.2 | 29.5 |
| 18 | 72.0 | 67.7 |
| 19 | 59.3 | 43.4 |
| 20 | 28.7 | 60.6 |
| 21 | 30.9 | 55.6 |
| 22 | 40.7 | 63.9 |

According to Table III, compounds of the invention are either active on MiaCaPa and/or Capan-2 cell lines. For example:

- compound n° 14 exhibits more than 50% of inhibition on both cell types.
- compound n° 15 exhibits more than 50% of inhibition on both cell types.
- compound n° 16 exhibits more than 50% of inhibition on both cell types.
- compound n° 17 is more potent on chemo-resistant and fast-growing MiaPaCa-2 cells.
- compound n° 18 exhibits more than 50% of inhibition on both cell types.
- compound n° 19 is more potent on chemo-resistant and fast-growing MiaPaCa-2 cells but also exhibits a moderate inhibition activity on chemo-sensitive and slow-growing Capan-2 cells.
- compound n° 20 is more potent on chemo-sensitive and slow-growing Capan-2 cells.
- compound n° 21 is more potent on chemo-sensitive and slow-growing Capan-2 cells.
- compound n° 22 is more potent on chemo-sensitive and slow-growing Capan-2 cells but also exhibits a moderate inhibition activity on chemo-resistant and fast-growing MiaPaCa-2 cells.

Further experiments (see B. and C. below) have been carried out in order to demonstrate the superiority of the compounds according to the invention compared to gemcitabine.

B. DOSE-DEPENDENCE EFFECTS OF SOME COMPOUNDS ACCORDING TO THE INVENTION ON CELL SURVIVAL (FIGS. 1, 2, 4 AND 5)

Cells were seeded on 96-well plates in 250 µL media and 24 hours later, compound to be tested was added in 250 µL of media to the desired final concentration (from 10 nM to 200 µM). After 48 hours, the number of viable cells remaining after the appropriate treatment was determined by MTT. Minimum Efficient Dose (MED) and IC$_{50}$ values was evaluated from the dose-dependency study. The results in FIGS. 1, 2, 4 and 5 are presented in percentage of cell growth inhibition compared to control non treated cells.

Results of tested compounds according to the present invention, i.e. compounds n° 1 and 4, for chemo-resistant and fast-growing MiaPaCa are shown in FIG. 1:
- at 50 μM of compounds n° 1 or 4, about 60% of cells die, and
- at 100 μM of compounds n° 1 or 4, more than 80% of cells die,
- whereas at 50 μM or 100 μM of gemcitabine, cell viability stagnates and about 80% of cells remains alive, independtly of dose increase.

Figure 2:
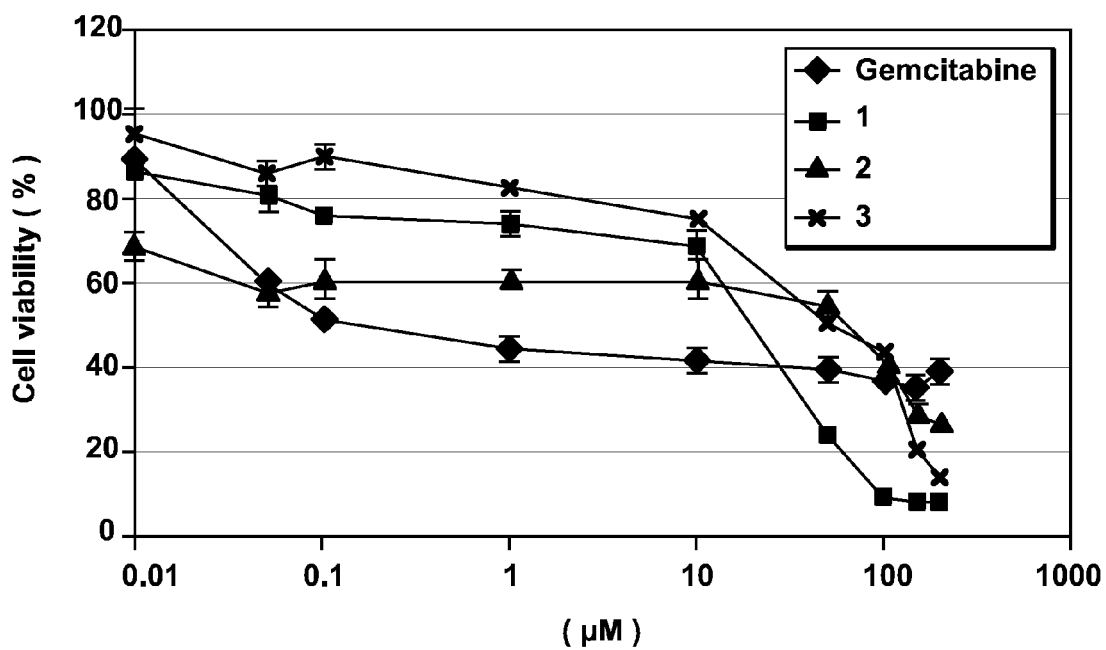
FIG. 2 illustrates the results of dose-dependency study on Capan-2 cells for some compounds according to the invention, compounds n° 1, 2 and 3, compared to gemcitabine.

Results of tested compounds according to the present invention, i.e. compounds n° 1, 2 and 3, for chemo-sensitive and slow growing Capan-2 are shown in FIG. 2:
- at 50 μM of compound n° 1, about 60% of cells die,
- at 100 μM of compound n° 1, more than 80% of cells die and for doses higher than 100 μM of compounds n° 2 or 3 cell viability rapidly decreases, whereas with gemcitabine cell viability stagnates independently of dose increase.

Figure 4:
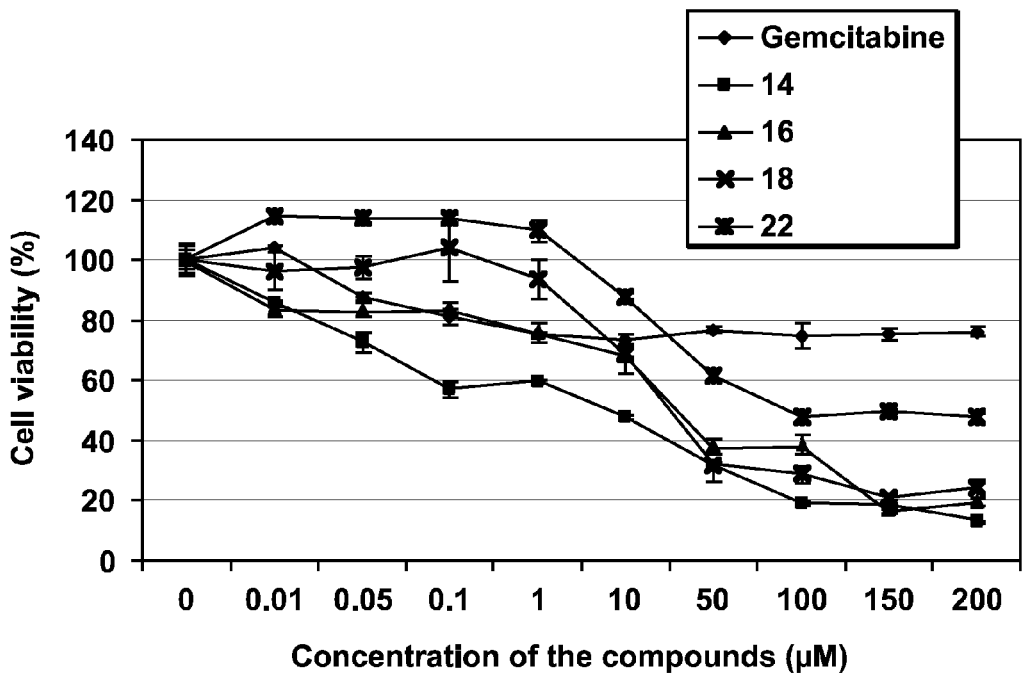
FIG. 4 illustrates the dose-dependence effects of the active compounds (14, 16, 18, 22) for MiaPaCa-2.
Figure 5:
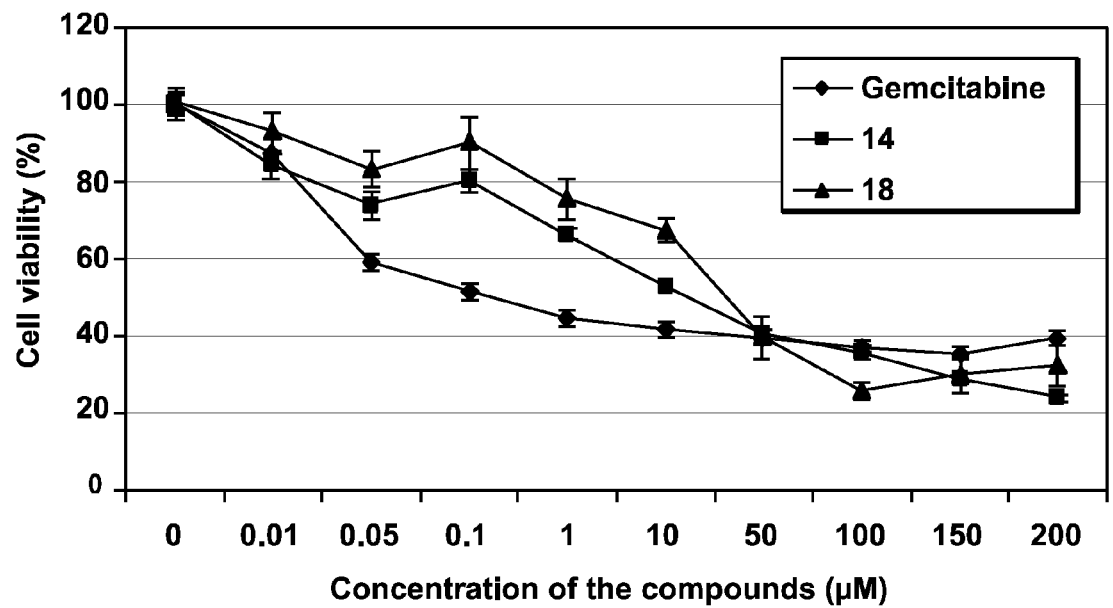
FIG. 5 illustrates the dose-dependence effects of active compounds (14, 18) for Capan-2.

Dose-dependence effects of the active compounds (14, 16, 18, 22) for MiaPaCa-2 are shown in FIG. 4, and active compounds (14, 18) for Capan-2 are shown in FIG. 5.

Consequently, compounds of the invention are active against cancer cells, such as chemo-resistant and fast-growing MiaPaCa cells and chemo-sensitive and slow-growing Capan-2 cells and thus constitute promising active principles for treating cancers, and in particular for treating cancers against which known drugs such as gemcitabine, have little impact and/or against which patients develop resistance.

C. APOPTOSIS EVALUATION OF COMPOUNDS ACCORDING TO THE INVENTION ON MIAPACA CELLS BY FLOW CYTOMETRY (FIGS. 3 AND 6), BY CASPASE 3/7 CLEAVAGE ASSAY (FIG. 7), AND BY ELISA ASSAY (FIG. 8)

Figure 3:
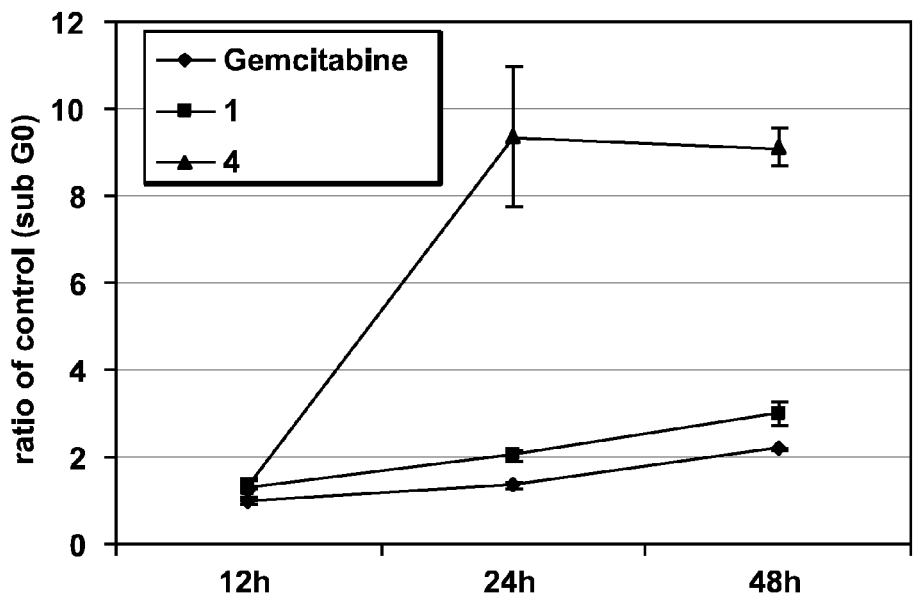
FIG. 3 illustrates the results of apoptosis study on MiaPaCa cells for some compounds according to the invention, compounds n° 1 and n° 4, compared to gemcitabine.

Cells were plated in 10 cm dishes at the density of 300 000 cells/plate. Cells were stopped for flow cytometry analysis 12, 24 and 48 h post-treatment. After trypsination, cell pellet was washed with PBS and fixed in cold-ethanol 70% overnight at 4° C. After a wash with phosphate-citrate buffer, cells were treated with 200 μL RNA-ase (500 μg/mL), labeled with 1 mL propidium iodide (50 μg/mL), and immediately analyzed by flow cytometry (FACS Calibur, Becton Dickinson, Le Pont-De-Claix, France). Cell death analysis was done on 1,000,000 cells, evaluating the sub-G0 ratio. Each sample was performed in triplicate. FIG. 3 shows the ratio of apoptotic rate compared to non treated control cells.

For the compounds according to the invention, this ratio is higher than with gemcitabine. This ratio is particularly high with compound n° 1 according to the instant invention. Actually, 24 h after administration, apoptosis is about 8 times higher compared to non-treated cells and about 4 times higher compared to cells treated with gemcitabine.

Figure 6:
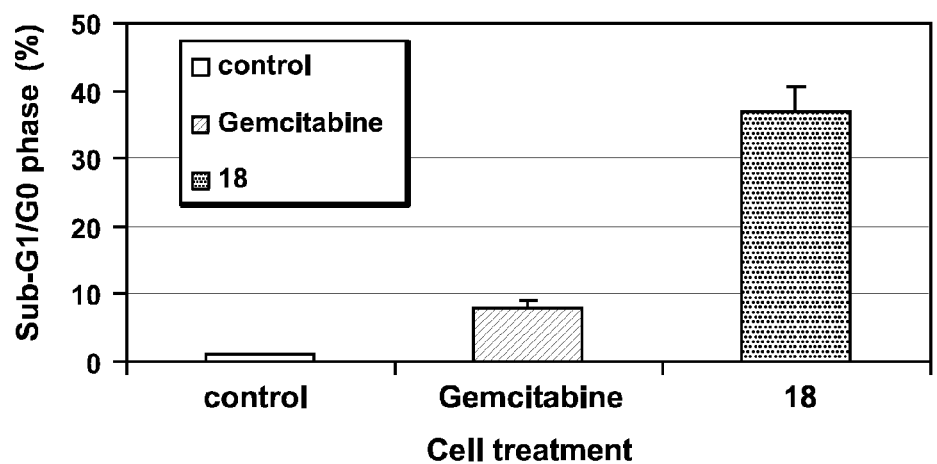
FIG. 6 illustrates the apoptosis evaluation of active MiaPaCa-2's (18) by flow cytometry.

Apoptosis evaluation of active MiaPaCa-2's (18) by flow cytometry is represented on FIG. 6.

Figure 7:
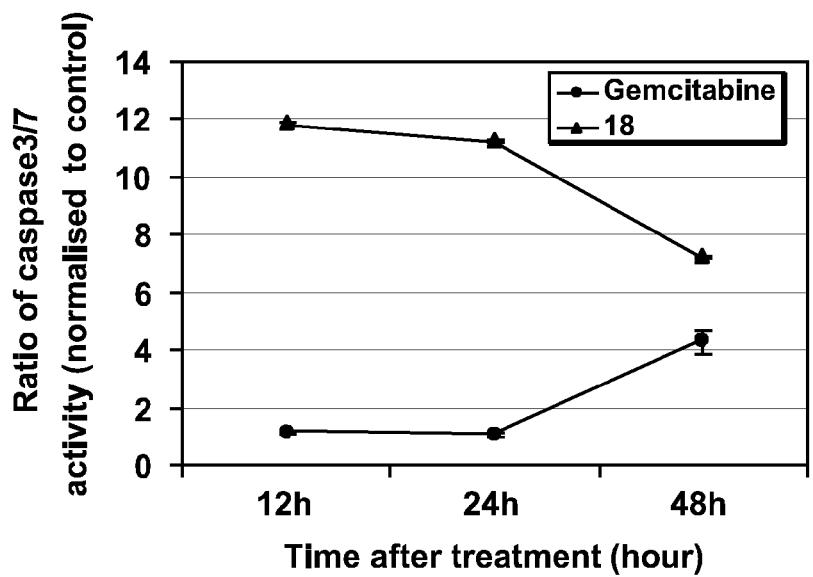
FIG. 7 illustrates the apoptosis evaluation of active MiaPaCa-2's (18) by Caspase-3/7 cleavage assay.
Figure 8:
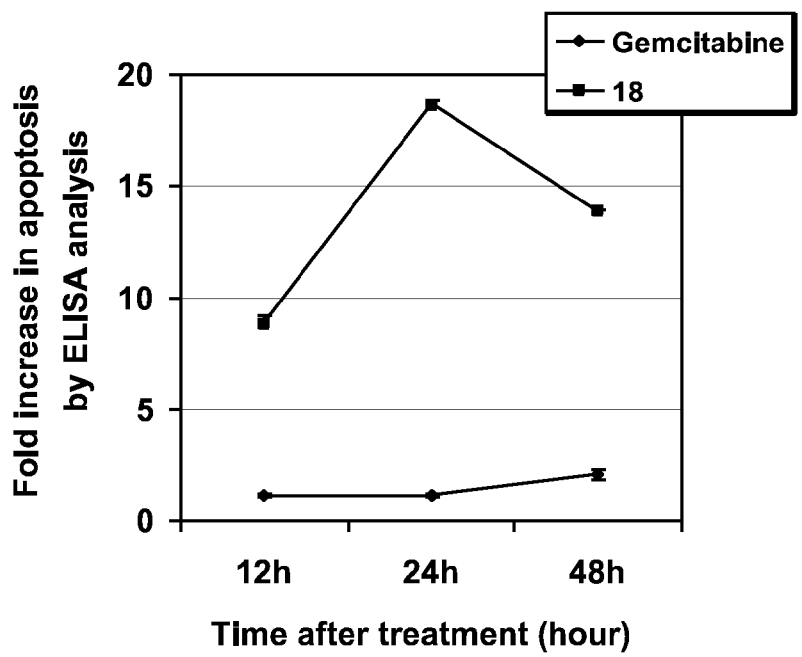
FIG. 8 illustrates the apoptosis evaluation of active MiaPaCa-2's (18) by an ELISA assay.

FIG. 7 represents a Caspase-3/7 cleavage assay on MiaPaCa with compound n° 18. Caspase-3/7 activity was measured using the Apo-ONE Homogeneous Caspase-3/7 Assay Fluorometric Kit (Promega). MiaPaCa-2 cells were initially seeded at 15,000 cells/well on 96-well plates. Twenty-four hours later, cells were treated with the test compound for 48 h and caspase-3 activity was measured by the cleavage of the fluorometric substrate Z-DEVD-R110 according to the instructions of the manufacturer (Promega). Next 100 μL of Apo-ONE Homogeneous Caspase-3/7 Reagent was added to each well of a black 96-well plate containing 100 μL of blank, control or cells in culture. Each experiment was performed in triplicate. The plate was covered with a plate sealer, incubated at room temperature for 30 minutes before measuring the fluorescence of each well.

The apoptosis was also assessed by an enzyme linked immunoassay (ELISA) that quantifies cytoplasmic nucleosomes produced during apoptosis (Cell Death Detection ELISA plus, Roche). Cells were seeded for 24 h in 96-well plates (15,000 cells/well) and treated by test compounds or not as negative control. After 48 h, the 96-well plates were centrifuged (200 g) for 10 min, the supernatant was discarded, and lysis buffer was added. After lysis, the samples were centrifuged and 20 μL of the supernatant transferred to a streptavidin-coated microtiter plate. Biotin-labeled antihistone antibodies and peroxidase conjugated anti-DNA antibodies were added to each well and the plate was incubated at room temperature for 2 h. After three washes with buffer, the peroxidase substrate was added to each well to quantitate the captured nucleosomes. After 20 min incubation, the plates were read at 405/490 nm in a microplate reader. The enrichment in histone-DNA fragments is expressed as a fold increase in absorbance compared with control. The results are set out in FIG. 8.

Dose dependency study and apoptosis study (experiments B. and C.) demonstrate that the compounds of the present invention show significant proliferation inhibition and apoptosis increase in cancer cells, compared to non-treated cells and to cells treated with gemcitabine.

D. BENEFICIAL COMBINATION EFFECT WITH GEMCITABINE IN VITRO

Figure 9:
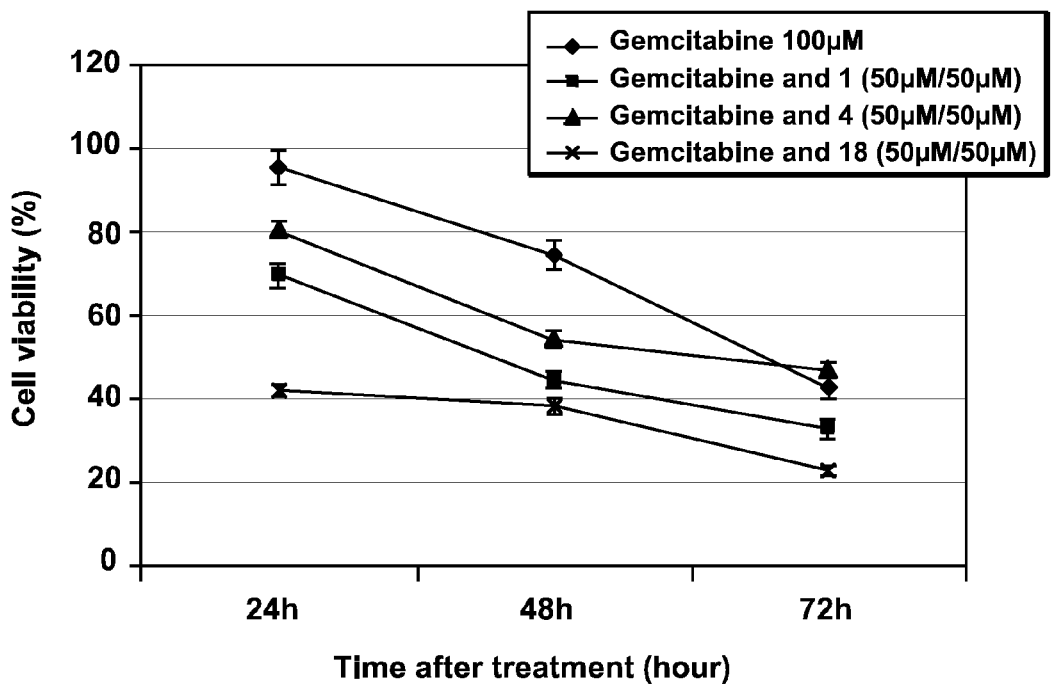
FIG. 9 illustrates the beneficial combination effect of compounds (1, 4 or 18) in vitro based on the results obtained by using a MTT assay on MiaPaCa-2 cells.

Three compounds (compounds n° 1, 4 and 18) combined with gemcitabine were accessed their anticancer activity. FIG. 9 showed that the combination of gemcitabine with 1 or 18 displayed more efficiency on antiproliferation.

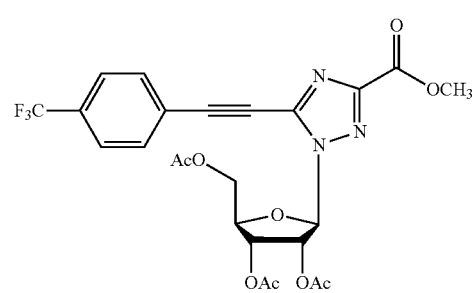

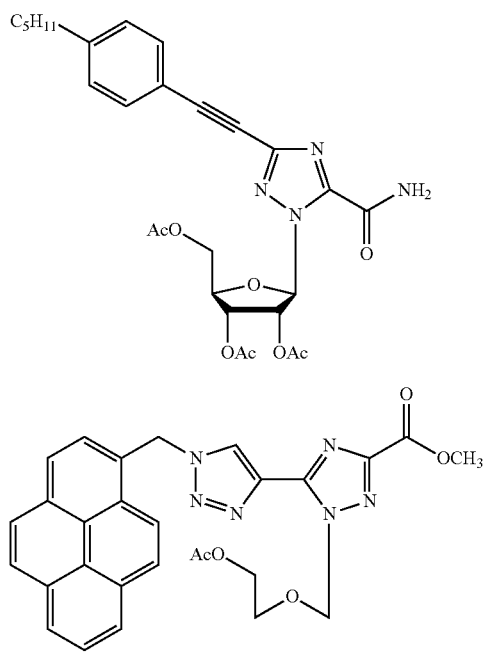

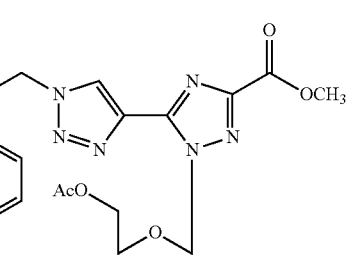

E. EFFECT OF DRUG TREATMENT ON MIAPACA-2 TUMOR GROWTH IN VIVO

The antitumor effects of the active compounds 1 and 4 were evaluated in nude mice bearing MiaPaCa-2-xenografed tumors. Institutional guidelines for the proper and human use of animals in research were followed. Approximately $1 \times 10^7$ MiaPaCa-2 cells were inoculated subcutaneously with 0.1 mL of Matrigel (BD Biosciences Discovery Labware) to 6-week-old male xenografed nude mice. When MiaPaCa-2 tumors reached 100 mm$^3$, mice were randomly selected for treatment with test compound and no treated mice were used as control. Each experimental group consisted of 8 mice. After randomization, 150 mg/kg test compound was injected every three days by i.p. injection for 5 weeks. The combination injection was performed every two days. Tumor volume measurements were performed once weekly and calculated by the formula length×width×depth×0.5236.

Figure 10:
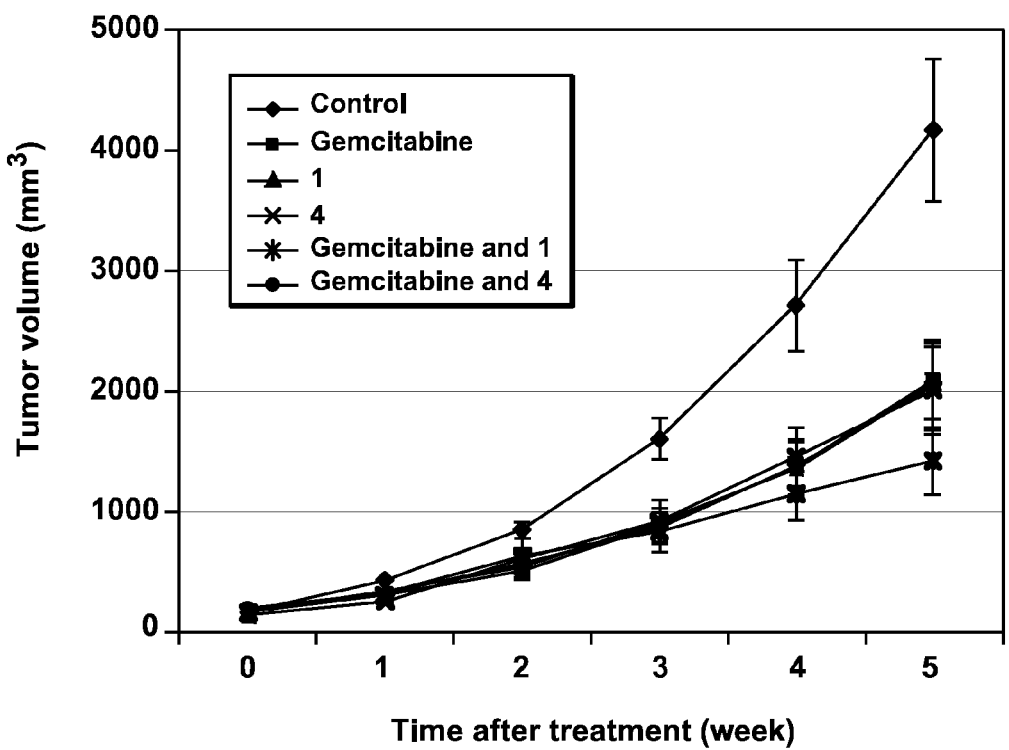
FIG. 10 illustrates the effect of drug treatment with compounds (1 or 4) alone or in combination with gemcitabine, on MiaPaCa-2 tumor growth in vivo.
Figure 11:
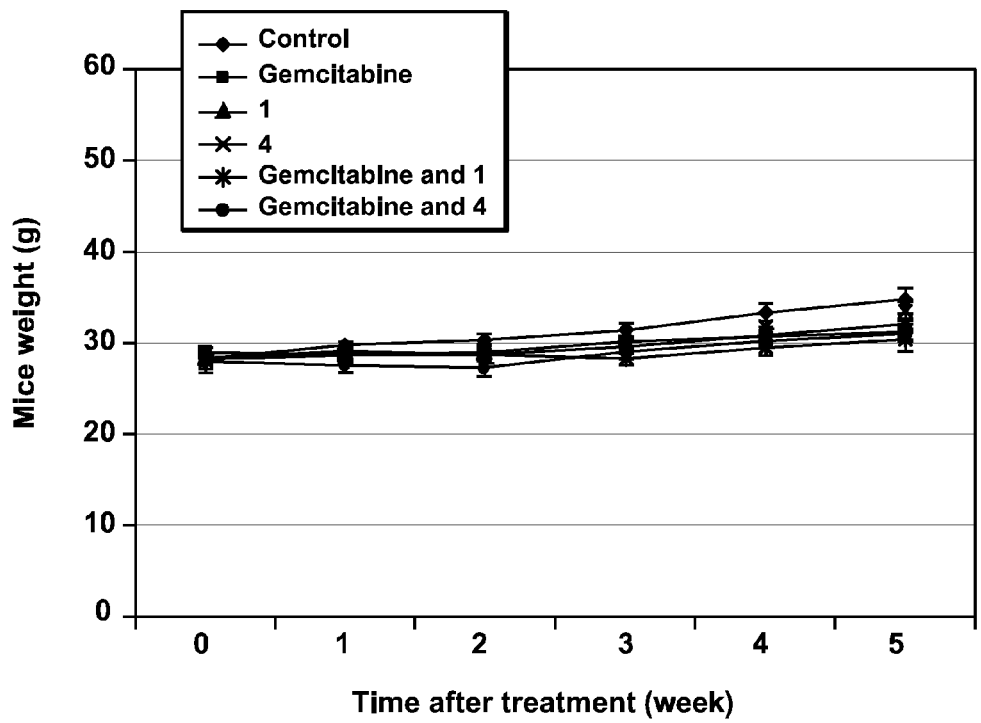
FIG. 11 illustrates the absence of adverse effect of drug treatment with compounds (1 or 4) alone or in combination with gemcitabine.

FIG. 10 shows that treatment with 1 and 4 could reduce MiaPaCa-2 tumor volume. Specially, tumor growth was almost sinificantly inhibited when 1 was combined with gemcitabine. Under the experimental conditions used, no adverse effects were observed (FIG. 11).

F. IDENTIFICATION OF THE INTRACELLULAR TARGETS OF THE COMPOUNDS

The stress-associated protein, p-8 with antiapoptotic properties was strongly expressed in two of the most resistant pancreactic cancer cell lines, while Heat Shock Protein 27 (Hsp27) is a protein which can be over-expressed in many tumor cells and protects against apoptotic cell death triggered by various stimuli. So in order to study the intracellular target of the active compounds, the effect of the active compounds on the expression of p-8 and Hsp27 mRNA in MiaPaCa-2 cells were investigated by quantitative RT-PCR. First-strand cDNA was synthesized in 20 μL reaction with 1 μg total RNA using Expand Reverse Transcriptase (Roche, Meylan, France) following the instructions of the manufacturer. Quantitative PCR was done with the Light Cycler system (Roche) and Takara (Berkeley, Calif.) reagents. Five microliters of 10-fold diluted cDNA were mixed with 10 μL SYBR Premix Ex Taq (including Taq polymerase, reaction buffer, MgCl$_2$, SYBR green I dye, and deoxynucleotide triphosphate mix) and 4 nmol forward and reverse primers (TBP primers are used as a control) in a volume of 20 μL. After an initial Taq activation for 10 seconds at 95° C., Light Cycler PCR was done using 45 to 55 cycles with the following cycling conditions: 95° C. for 5 seconds, 58° C. for 6 seconds, and 72° C. for 12 seconds. Each sample was analyzed in duplicate and the experiment was repeated twice. Results were analyzed using RelQuant (Roche) and expressed as percent of control values.

Figure 12:
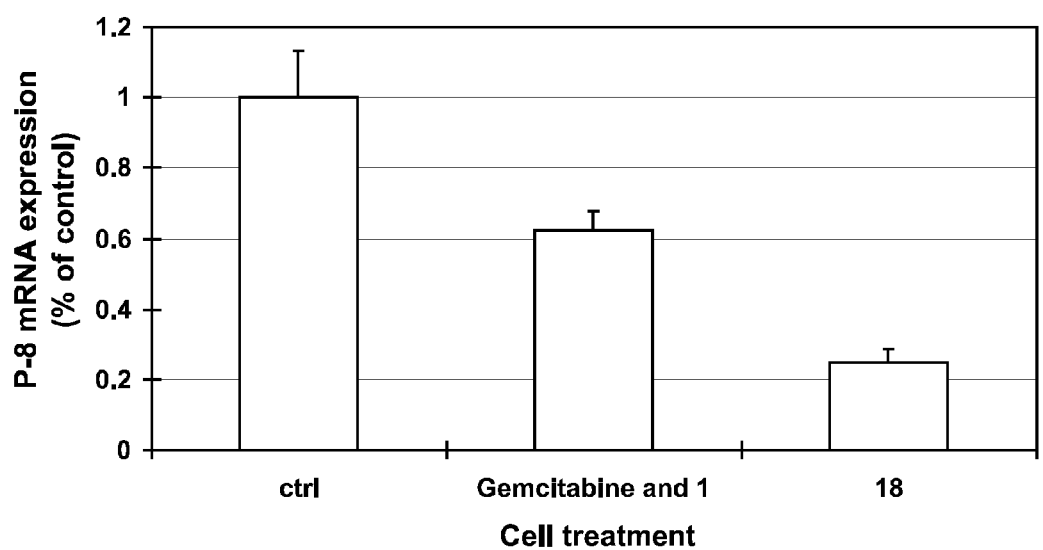
FIG. 12 illustrates the down-regulation effect of p-8 mRNA expression by compound 1 together with gemcitabine, and compound 18 alone.

FIG. 12 showed that p-8 mRNA expression was down-regulated by the combination of gemcitabine and 1. Especially here, the single treatment of compound 18 can significantly inhibit the expression of p-8.

Figure 13:
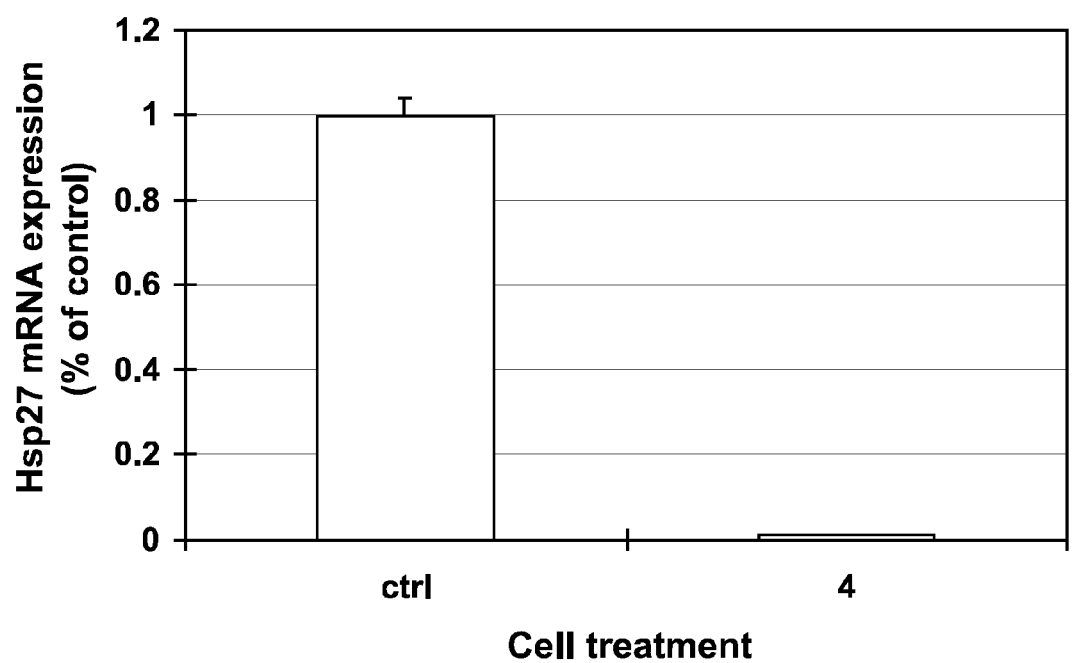
FIG. 13 illustrates the inhibition of Hsp27 mRNA expression in MiaPaCa-2 cells by compound 4.

FIG. 13 indicated that Hsp27 mRNA expression in MiaPaCa-2 cells was almost completely inhibited by the treatment of 4.

Hence, the invention provides new compounds which show significant proliferation inhibition and apoptosis increase in pancreatic cancer cells. The above in vivo test of the active compounds confirmed that these compounds can inhibit the tumor growth in the animal model with no adverse effect. Further, the above results show that the antiproliferation effect on cancer cells of the active compounds may be related to their ability of inhibition of the expression of the anti-apoptotic protein p-8 and Hsp27.

Compounds according to the invention represent low toxicity cancer preventive and/or therapeutic agents, useful for the preparation of a composition intended to treat and/or prevent cancers in a mammal, including a human.

Thus an object of the invention relates to a compound according to the present invention for use for preventing and/or treating cancers such as brain tumor, medulloblastoma, glioma, pituitary tumor, neuroglia, acoustic neuroma, pharyngeal cancer, laryngeal cancer, tongue cancer, thymoma, mesothelioma, breast cancer, lung cancer, non-small cell lung cancer, small cell lung cancer, gastric cancer, esophageal cancer, colorectal cancer, colon cancer, rectal cancer, liver cancer, hepatocellular carcinoma, pancreatic cancer, pancreatic endocrine tumor, bile duct cancer, gallbladder cancer, penile cancer, renal cancer, renal pelvic cancer, urethral cancer, renal cell cancer, testicular tumor, prostate cancer, bladder cancer, vulvar cancer, uterine cancer, cervical cancer, uterine body cancer, uterine sarcoma, trophoblastic disease, vaginal cancer, ovary cancer, ovarian germ cell tumor, skin cancer, malignant melanoma, mycosis fungoides, basalioma, soft part sarcoma, malignant lymphoma, Hodgkin's disease, myelodysplastic syndrome, multiple myeloma, leukemia, acute myeloid leukemia, chronic myeloid leukemia, acute lymphocytic leukemia, chronic lymphocytic leukemia, adult T-cell leukemia, chronic myeloproliferative disease, pancreatic endocrine tumor, unknown primary cancer, preferably, medulloblastoma, breast cancer, small cell lung cancer, gastric cancer, esophageal cancer, colorectal cancer, colon cancer, pancreatic cancer, bile duct cancer, prostate cancer.

A further embodiment of the instant invention is a compound of formula (A), notably of formula (I), (I') and (I"), for use in the treatment and/or prevention of cancers.

Another embodiment of the instant invention is a compound of formula (A), notably of formula (I), (I') and (I"), for use in the treatment and/or prevention of pancreatic cancer.

Compounds according to the invention can be used for the preparation of pharmaceutical compositions, specifically of medicaments, intended to treat and/or prevent the above-mentioned diseases.

Therefore, one aspect of the invention is a pharmaceutical composition which comprises, as active principle, at least one compound according to the present invention.

Such a pharmaceutical composition comprises an effective dose of at least one compound according to the invention, or an addition salt thereof with a pharmaceutically acceptable salt, or a hydrate or solvate of the latter, and at least one pharmaceutically acceptable excipient. Said excipients are chosen according to the pharmaceutical form and the administration route desired, among usual excipients known of one of skill in the art.

More particularly, the instant invention is directed to a medicament, comprising a compound of formula (A), notably of formula (I), (I') and (I"), or an addition salt of said compound to a pharmaceutically acceptable salt, or a hydrate or solvate of a compound of formula (A), notably of formula (I), (I') and (I").

In the pharmaceutical compositions according to the invention for the oral, sublingual, sub-cutaneous, intramuscular, intra-venous, topical, local, intratracheal, intranasal, trans-dermal or rectal administration, the active principle of formula (A), notably of formula (I), (I') and (I"), above, its salt, solvate or hydrate, can be administered as a unitary dosage form, in blend with usual pharmaceutical excipients, to animals and human beings for the prevention or for the treatment of diseases mentioned above.

The appropriate unitary dosage forms comprise the oral forms, such as tablets, hard or soft gelatin capsules, powders, granules and oral solutions or suspensions, the sublingual, buccal, intratracheal, intraocular, intranasal forms, by inhalation, the topical, transdermal, sub-cutaneous, intramuscular or intra-venous forms, the rectal forms and the implants. For the topical application, the compounds of the invention may be used as creams, gels, ointments or lotions.

As an example, a unitary dosage form for a compound according to the invention, in the form of a tablet, can comprise the following ingredients:

| | |
|---|---|
| Compound according to the invention | 50.0 mg |
| Mannitol | 223.75 mg |
| Croscarmellose sodique | 6.0 mg |
| Maize starch | 15.0 mg |
| Hydroxypropyl methylcellulose | 2.25 mg |
| Magnesium stearate | 3.0 mg |

By the parenteral route, the dose may for example reach 150 mg/kg/day.

Depending on the administration route and on the patient, higher or lower dosages may be appropriate. These dosages are comprised within the scope of the present invention.

The present invention, according to another of its aspects, also relates to a method for the treatment of the above pathologies, which comprises the administration to a patient of an effective dose of a compound according to the invention, or a pharmaceutically acceptable salt thereof, or a hydrate or a solvate thereof.

Such a treatment comprises administering to the mammal in need of such treatment, a therapeutically effective amount of the compound of formula (A), notably of formula (I), (I') and (I"), as an active ingredient.

The present invention further relates to the use of a composition according to the invention for separate, combined or sequential use in the treatment of cancer, comprising:
a) administering to a patient an effective amount of at least one or more compounds of formula (A), notably of formula (I), (I') and (I"), and optionally
b) further administering an effective amount of one or more compounds effective in the treatment of cancers.

In this case, the further active agent which is co-administered with a compound according to the instant invention, may be for example other molecules with anticancer or cytostatic properties, such as platine salts, antracyclines, mitotic taper poison, topoisomerase inhibitors, kinases inhibitors of topoisomerase inhibitors. As an example, the further active agent may be gemcitabine. The association with hyperthermy which is used in some chemotherapies may be considered.

The compounds according to the instant invention may also be used in combination with other cytotoxic agents, molecular therapies, surgical therapies and/or with radiations for the treatment of cancers.

What is claimed is:
1. A compound of general formula (I) or (I"):

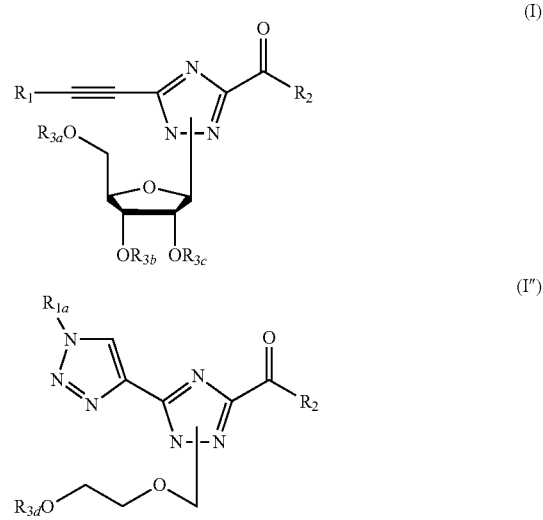

wherein:
$R_1$ and $R_{1a}$ represent a radical $C_{1-18}$alkyl, $C_{2-18}$alkenyl, $C_{3-10}$cycloalkyl, $C_{3-10}$cycloalkyl-$C_{1-6}$alkylene, $C_{3-10}$cycloalkenyl, $C_{6-20}$aryl, $C_{5-14}$aryl-$C_{1-6}$alkylene, $C_{3-10}$heterocyclyl, $C_{3-10}$heterocyclyl-$C_{1-6}$alkylene, $C_{5-20}$heteroaryl or $C_{5-20}$heteroaryl-$C_{1-6}$alkylene, said radicals being optionally substituted with one or more $R_4$;

$R_2$ represents —$NH_2$, —$NHR_5$, a hydroxyl or a $C_{1-6}$alkoxy group;

$R_{3a}$, $R_{3b}$, $R_{3c}$ and $R_{3d}$ represent independently from each other a hydrogen atom, a $C_{1-18}$alkyl, $C_{2-18}$alkenyl, $C_{6-20}$aryl or —$C(O)R_5$;

$R_4$ represents a halogen atom, a hydroxyl, —$NH_2$, —$NHR_5$, —$NO_2$, —$CN$, —$CF_3$, —$C(O)R_5$, a radical $C_{1-14}$alkyl, $C_{1-6}$alkoxy, $C_{2-6}$alkenyl, $C_{2-6}$alkynyl, $C_{6-20}$aryl, $C_{5-20}$heteroaryl or $C_{5-14}$aryl-$C_{1-6}$alkylene;

$R_5$ represents $C_{1-18}$alkyl, $C_{2-18}$alkenyl, $C_{2-18}$alkynyl, $C_{5-14}$aryl, $C_{3-10}$heterocyclyl, $C_{5-20}$heteroaryl, $C_{5-14}$aryl-$C_{1-6}$alkylene, $C_{5-14}$aryl-$C_{2-18}$alkenylene, $C_{5-14}$aryl-$C_{2-18}$alkynylene, $C_{5-20}$heteroaryl-$C_{1-6}$alkylene, C$_{5-20}$heteroaryl-C$_{2-18}$alkenylene, C$_{5-20}$heteroaryl-C$_{2-18}$alkynylene, C$_{3-10}$heterocyclyl-C$_{1-6}$alkylene, C$_{3-10}$heterocyclyl-C$_{2-18}$alkenylene or C$_{3-10}$heterocyclyl-C$_{2-18}$alkynylene;

in the form of a free base or of an addition salt with an acid.

2. The compound of formula I according to claim 1, wherein R$_1$ represents a radical C$_{6-20}$aryl group, said radical being substituted with one or more group R$_4$; wherein R$_4$ represents a halogen atom, a —CF$_3$ group, a C$_{1-6}$ alkoxy or else a C$_{1-14}$ alkyl group 1.

3. The compound according to claim 1, represented by formula (II):

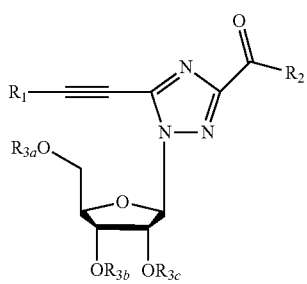

(II)

wherein R$_1$, R$_2$, R$_{3a}$, R$_{3b}$ and R$_{3c}$ are as defined in claim 1.

4. The compound according to claim 3, wherein in the compound of formula (II):

R$_1$ represents a radical C$_{6-20}$ aryl, said radical being substituted with one or more R$_4$;

R$_4$ represents a —CF$_3$ or a C$_{1-14}$alkyl group;

R$_2$ represents —NH$_2$ or a C$_1$-C$_6$alkoxy group;

R$_{3a}$, R$_{3b}$ and R$_{3c}$ represent independently from each other a hydrogen atom, or a —C(O)R$_5$; R$_5$ being a C$_1$-C$_6$alkyl group.

5. The compound according to claim 4, wherein R$_1$ is substituted with one R$_4$ and R$_4$ is in para position.

6. The compound according to claim 1, represented by a compound of formula (III):

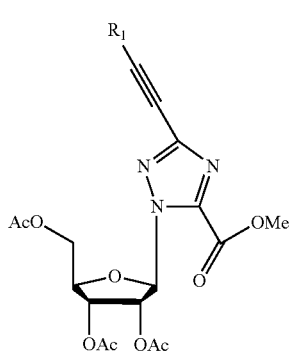

(III)

wherein R$_1$ is optionally substituted with one or more R$_4$, R$_1$ and R$_4$ as defined in claim 1.

7. The compound according to claim 1, represented by a compound of formula (IV):

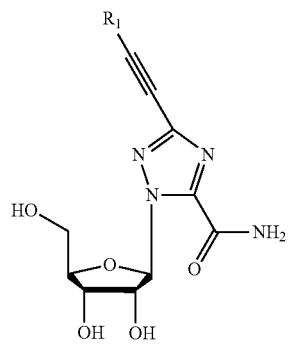

(IV)

wherein R$_1$ is optionally substituted with one or more R$_4$, R$_1$ and R$_4$ being as defined in claim 1.

8. The compound according to claim 7, wherein:
R$_1$ represents a radical C$_{1-18}$alkyl, a C$_{6-20}$aryl, C$_{3-10}$cycloalkyl or a C$_{3-10}$cycloalkenyl, said radicals being optionally substituted with one or more R$_4$.

9. The compound according to claim 7, wherein when R$_1$ represents a C$_{6-20}$ aryl, R$_1$ is substituted with one R$_4$; R$_4$ representing a halogen atom, a —CF$_3$, a C$_{1-14}$alkyl group or a C$_{1-6}$ alkoxy group.

10. The compound according to claim 1, wherein the compound of formula (I) is selected from the group consisting of:
Methyl 5-(4-trifluoromethylphenylethynyl)-1-(2,3,5-tri-O-acetyl-β-D-ribofuranosyl)-1H-[1,2,4]triazole-3-carboxylate;
Methyl 5-(Cyclohexenylethynyl)-1-(2,3,5-tri-O-acetyl-β-D-ribofuranosyl)-1H-[1,2,4]triazole-3-carboxylate;
5-(4-trifluoromethylphenylethynyl)-1-(2,3,5-tri-Hydroxy-β-D-ribofuranosyl)-1H-[1,2,4]triazole-3-carboxylic acid amide; and
3-(4-pentylphenylethynyl)-1-(2,3,5-tri-Hydroxy-β-D-ribofuranosyl)-1H-[1,2,4]triazole-5-carboxylic acid amide.

11. The compound of formula (I″) according to claim 1, represented by formula (II″):

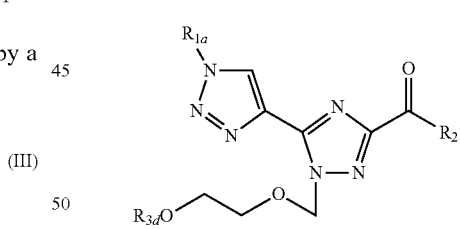

(II″)

wherein R$_{1a}$, R$_2$ and R$_{3d}$ are as defined in claim 1.

12. The compound of formula (II″) according to claim 11, wherein:
R$_{1a}$ represents a radical C$_{1-18}$alkyl, or C$_{5-14}$aryl-C$_{1-6}$alkylene;
R$_2$ represents —NH$_2$ or a C$_1$-C$_6$alkoxy group;
R$_{3d}$ represents a hydrogen atom or a —C(O)R$_5$; R$_5$ being a C$_{1-18}$ alkyl group.

13. The compound of formula (II″) according to claim 12, which is selected from the group consisting of:
1-((2-hydroxyethoxy)methyl)-5-(1-dodecyl-1H-1,2,3-triazol-4-yl)-1H-1,2,4-triazole-3-carboxamide;
Methyl 1-((2-acetoxyethoxy)methyl)-5-(1-((pyren-3-yl)methyl)-1H-1,2,3-triazol-4-yl)-1H-1,2,4-triazole-3-carboxylate;

1-((2-hydroxyethoxy)methyl)-5-(1-((pyren-3-yl)methyl)-1H-1,2,3-triazol-4-yl)-1H-1,2,4-triazole-3-carboxamide;

1-((2-hydroxyethoxy)methyl)-3-(1-((pyren-3-yl)methyl)-1H-1,2,3-triazol-4-yl)-1H-1,2,4-triazole-5-carboxamide;

1-((2-hydroxyethoxy)methyl)-5-(1-(naphthalen-1-yl)-1H-1,2,3-triazol-4-yl)-1H-1,2,4-triazole-3-carboxamide; and Methyl 1-((2-acetoxyethoxy)methyl)-5-(1-(pyren-3-yl)-1H-1,2,3-triazol-4-yl)-1H-1,2,4-triazole-3-carboxylate.

14. A process for the preparation of a compound of formula (I), according to claim 1 wherein:

a compound of formula (VI):

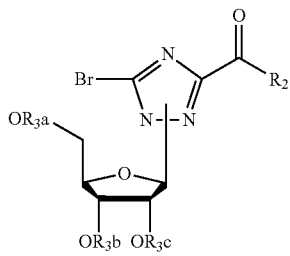

(VI)

wherein $R_2$, $R_{3a}$, $R_{3b}$ and $R_{3c}$ are as described for the compounds of formula (I), is reacted with a compound of formula (V):

(V)

wherein $R_1$ is as described for the compound of formula (I) according to Pd-catalyzed Sonogashira coupling reaction under microwave irradiation.

15. A medicament comprising a compound of formula (I) or (I") according to claim 1 or an addition salt of said compound to a pharmaceutically acceptable salt of said compound.

16. A pharmaceutical composition, comprising at least one compound of formula (I) or (I") according to claim 1 or an addition salt of said compound to a pharmaceutically acceptable salt and at least one pharmaceutically acceptable excipient.

17. A method of treating pancreatic cancer comprising:

administering the compound according to claim 1 to a mammal in need of treatment of pancreatic cancer.

\* \* \* \* \*

UNITED STATES PATENT AND TRADEMARK OFFICE
CERTIFICATE OF CORRECTION

Page 1 of 2

PATENT NO. : 8,563,526 B2
APPLICATION NO. : 12/990214
DATED : October 22, 2013
INVENTOR(S) : Peng et al.

It is certified that error appears in the above-identified patent and that said Letters Patent is hereby corrected as shown below:

In the Specification

In column 1 at line 27, Change "formule" to --formulae--.

In column 2 at line 28 (approx.), Change "others" to --other--.

In column 3 at line 13 (approx.), Change "asymetric" to --asymmetric--.

In column 3 at line 38, Change "meanings." to --meanings:--.

In column 4 at line 23, Change ""cycloalkynyl"corresponds" to --"cycloalkynyl" corresponds--.

In column 4 at line 45, Change "dihydroypyridyl," to --dihydroxypyridyl,--.

In column 5 at line 23, Change "alkynylene"," to --alkynylene".--.

In column 5 at line 26, Change "an" to --a--.

In column 6 at line 43 (approx.), Change "others" to --other--.

In column 7 at line 29, Change "ore" to --or--.

In column 7 at line 36, Change "$C_6$-$C_{20}$ aryl" to --$C_6$-$C_{20}$aryl--.

In column 8 at line 25, Change "(3" to --β--.

In column 8 at line 56, Change "1H[1,2,4]" to --1H-[1,2,4]--.

In column 8 at line 58, Change "(3-D" to --β-D--.

In column 8 at line 64, Change "(3-D" to --β-D--.

In column 8 at line 67, Change "(3-D" to --β-D--.

In column 9 at line 4, Change "(3-D" to --β-D--.

In column 10 at line 56, Change "$R_{1c}$" to --$R_{3c}$--.

In column 12 at line 41 (approx.), Change "bromo-[2,3,5" to --bromo-1-[2,3,5--.

In column 12 at line 62, Change "$H_{Z1}$ 123.8," to --$H_Z$ 123.8,--.

In column 13 at line 31, Change "1H[1,2,4]" to --1H-[1,2,4]--.

In column 14 at line 29, Change "NH2)," to --$NH_2$),--.

Signed and Sealed this
Twenty-fourth Day of June, 2014

Michelle K. Lee
*Deputy Director of the United States Patent and Trademark Office*

CERTIFICATE OF CORRECTION (continued)
U.S. Pat. No. 8,563,526 B2

In column 15 at line 29, Change "J1" to --$J_1$--.

In column 17 at line 21, Change "$^1$HNMR" to --$^1$H NMR--.

In column 17 at line 24, Change "$C_{14}H_{14}N_4BrO_3^+$365.0244," to --$C_{14}H_{14}N_4BrO_3^+$ 365.0244,--.

In column 17 at line 50, Change "$^{13}$CNMR" to --$^{13}$C NMR--.

In column 17 at line 55, Change "cm⁻)" to --$cm^{-1}$).--.

In column 18 at line 10, Change "$^{13}$CNMR" to --$^{13}$C NMR--.

In column 18 at line 18, Change "methyl-5" to --methyl)-5--.

In column 18 at line 28, Change "cosumption" to --consumption--.

In column 18 at line 30, Change "puried" to --purified--.

In column 18 at line 47, Change "$^{13}$CNMR" to --$^{13}$C NMR--.

In column 19 at line 4, Change "$^1$HNMR" to --$^1$H NMR--.

In column 19 at line 8, Change "$^{13}$CNMR" to --$^{13}$C NMR--.

In column 19 at line 29, Change "d6):" to --$d_6$):--.

In column 19 at line 34, Change "$^{13}$CNMR" to --$^{13}$C NMR--.

In column 19 at line 51, Change "$^1$HNMR" to --$^1$H NMR--.

In column 20 at line 1, Change "$^1$HNMR" to --$^1$H NMR--.

In column 20 at line 6, Change "$^{13}$CNMR" to --$^{13}$C NMR--.

In column 20 at line 10, Change "402.1293" to --402.1293.--.

In column 20 at line 22, Change "$^1$HNMR" to --$^1$H NMR--.

In column 20 at line 26, Change "$^{13}$CNMR" to --$^{13}$C NMR--.

In column 21 at line 12, Change "Pancreactic" to --Pancreatic--.

In column 21 at line 14, Change "densitiy" to --density--.

In column 21 at line 19, Change "densitiy" to --density--.

In column 22 at line 6, Change "cells," to --cells.--.

In column 23 at lines 15-16, Change "independtly" to --independently--.

In column 23 at line 48, Change "trypsination," to --trypsinization--.

In column 25 at line 34, Change "xenografed" to --xenografted--.

In column 25 at line 39, Change "xenografed" to --xenografted--.

In column 25 at line 50, Change "sinificantly" to --significantly--.

In column 25 at line 59, Change "pancreactic" to --pancreatic--.

In the Claims

In column 29 at line 11, In Claim 2, change "group 1." to --group.--.